(12) United States Patent
Schlessinger et al.

(10) Patent No.: US 6,803,452 B2
(45) Date of Patent: Oct. 12, 2004

(54) RPTP-β ANTIBODIES

(75) Inventors: Joseph Schlessinger, New York, NY (US); Gilad Barnea, New York, NY (US)

(73) Assignee: New York University, New York, NY (US)

( * ) Notice: Subject to any disclaimer, the term of this patent is extended or adjusted under 35 U.S.C. 154(b) by 221 days.

(21) Appl. No.: 10/000,954

(22) Filed: Dec. 4, 2001

(65) Prior Publication Data
US 2002/0127226 A1 Sep. 12, 2002

Related U.S. Application Data

(63) Continuation of application No. 09/644,293, filed on Aug. 23, 2000, now abandoned, which is a division of application No. 08/081,929, filed on Jun. 23, 1993, now Pat. No. 6,160,090, which is a continuation-in-part of application No. 07/961,235, filed on Oct. 15, 1992, now abandoned, and a continuation-in-part of application No. 08/015,973, filed on Feb. 10, 1993, now Pat. No. 5,604,094, which is a continuation-in-part of application No. 07/654,188, filed on Feb. 26, 1991, now abandoned.

(51) Int. Cl.$^7$ .................... C07K 16/00; C07K 1/00; C07K 14/00; C07K 17/00; A61K 38/00
(52) U.S. Cl. .............. 530/387.1; 530/300; 530/350
(58) Field of Search .................... 530/387.1, 300, 530/350

(56) References Cited

PUBLICATIONS

Kaplan R et al. Proc. Natl. Acad. Sci. USA 87(18):7000–7004, 1990.*
Krueger et al. the EMBO J. 9(10):3241–3252, 1990.*
Sap et al. Proc. Natl. Acad. Sci. USA 87:6112–6116, 1990.*
Kiang, W.–L. et al., 1981, J. Biol. Chem. 256:10529–10537.
Hoffman, S. et al., 1982, J. Biol. Chem. 257:7720–7729.
Hoffman, S. and Edelman, G.M., 1983, Proc. Natl. Acad. Sci. USA 80:5762–5766.
Grumet, M. et al., 1984, Proc. Natl. Acad. Sci USA 81:267–271.
Thomas, M.L. et al., 1985, Cell 41:83–93.
Durst, M. et al., 1987, Proc. Natl. Acad. Sci USA 84:1070–1074.
Ralph, S.J. et al., 1987, EMBO J. 6:1251–1257.
Deutsch, H.F., 1987, Int. J. Biochem. 19:101–113.
Hunter, T., 1987, Cell 49:1–14.
Thomas, M.L. et al., 1987, Proc. Natl. Acad. Sci. USA 84:5360:5363.
Williams, A.F., 1987, Immunol. Today 8:298–303.
Honegger, A.M. et al., 1987 Cell 51:199–209.
Doege, K.M. et al., 1987, J. Biol. Chem. 262: 17757–17767.
Grumet, M. and Edelman, G.M., 1988, J. Cell Biol. 106:487–503.
Streuli, M. et al., 1988, J. Exp. Med. 168:1523–1530.
Ledbetter, J.A. et al., 1988, Proc. Natl. Acad. Sci. USA 85:8628–8632.
Margolis, B. et al., 1989, Cell 57:1101–1107.
Charbonneau, H. et al., 1989, Proc. Natl. Acad. Sci. USA 86:5252–5256.
Cool, D.E. et al., 1989, Proc. Natl. Acad. Sci. USA 86:5257:5261.
Moria, A.O. et al., 1989, Cell 58:193–203.
Hunter, T., 1989, Cell 58:1013–1016.
Streuli, M. et al., 1989, Proc. Natl. Acad. Sci. USA 86:8698–8702.
Hynes, R.O., 1990, Fibronectins, Springer–Verlag, New York.
Guan, K. et al., 1990, Proc. Natl. Acad. Sci. USA 87:1501–1505.
Krueger, N.X. et al., 1990, EMBO J.9:3241–3252.
Ullrich, A. and Schlessinger, J., 1990, Cell 61:203–212.
Hardie, D.G., 1990, Symp. Soc. Exp. Biol. 44:241–255.
Nurse, O., 1990, Nature 344:503–508.
Sap, J. et al., 1990, Proc. Natl. Acad. Sci. USA 87:6112–6116.
Kaplan, R. et al., 1990, Proc. Natl. Acad. Sci. USA 87:7000–7004.
Jirik, F.R. et al., 1990, FEBS Lett. 273:239–242.
Hunter T., 1991, Cell 64:249–270.
Fischer, E.H. et al., 1991 Science 253:401–406.
Cantley, L.C. et al., 1991, Cell 64:281–302.
Takeichi, M., 1991, Science 251:1451–1455.
Nada, S. et al., 1991, Nature 351:69–72.
LaForgia, S. et al., 1991, Proc. Natl. Acad. Sci. USA 88:5036–5040.
Cannizzano, L.A. et al., 1991, Cancer Res. 51:3818–3820.
Lombroso et al., 1991, Proc. Natl. Acad. Sci. USA 88:7242–7246.
Rauch, U. et al., 1991, J. Biol. Chem. 266:14785–14801.
Posada, J. and Cooper, J.A., 1992, Mol. Biol. Cell 3:583–592.
Schlessinger, J. and Ullrich, A., 19992, Neuron 9:383–391.
Scott, J.D. and Soderling, T.R., 1992, Current Opinion in Neurobiology 2:289–295.
Erickson, H.P., 1989, Ann. Rev. Cell Biol. 5: 71–92.

* cited by examiner

*Primary Examiner*—Robert Landsman
(74) *Attorney, Agent, or Firm*—Beth A. Burrous; Foley & Lardner LLP

(57) ABSTRACT

A new class of receptor protein tyrosine phosphatase molecule, the families of ligands that binds this new class of receptor, and uses of such receptors and ligands is described.

3 Claims, 19 Drawing Sheets

Figure 2A:
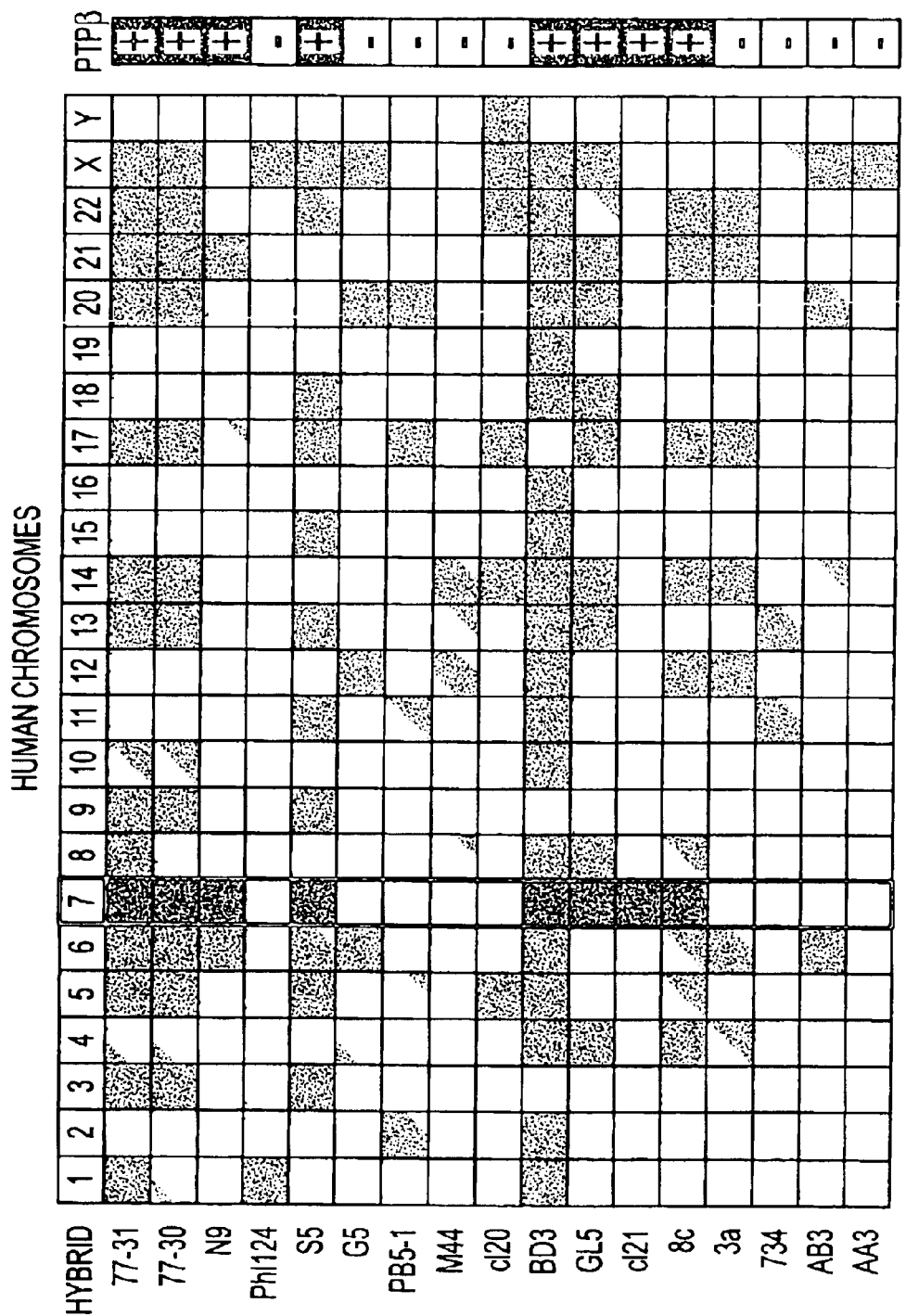

```
    MRILKRFLACIQLLCVRLDWANGYYRQQRKLVEEIGWSYTGALNQKNWGKKYPTCNSPKQSPINIDEDLTQVNVNLKKLKFQGWDKTSLENTFIHNTGK   CAH
101 TVEINLTNDYRVSGGVSEMVFKASKITTFHWGKCNMSSDGSEHSLEGQKFPLEMQIYCFDADRFSSFEEAVKGKGKLRALSILFEVGTEENLDFKAIIDGV
201 ESVSRFGKQAALDPFILLNLLPNSTDKYYIYNGSLTSPPCTDTVDWIVFKDTVSISESQLAVFCEVLTMQQSGYVMLMDYLQNNFREQQYKFSRQVFSSY
301 TGKEEIHEAVCSSEPENVQADPENYTSLLVTWERPRVVYDTMIEKFAVLYQQLDGEDQTKHEFLTDGYQDLGAILNNLLPNMSYVLQIVAICTNGLYGKY
401 SDQLIVDMPTDNPELDLFPELIGTEEIIKEEEGKDIEEGAIVNPGRDSATNQIRKKEPQISTTTHYNRIGTKYNEAKTNRSPTRGSEFSGKGDVPNTSL
501 NSTSQPVTKLATEKDISLTSQTVTELPHTVEGTSASLNDGSKTVLRSPHMNLSGTAESLNTVSITEYEEESLLTSFKLDTGAEDSSGSSPATSAIPFIS
601 ENISQGYIFSSENPETITYDVLIPESARNASEDSTSSGSEESLKDPSMEGNVWFPSSTDITAQPDVGSGRESFLQTNYTEIRVDESEKTTKSFSAGPVMS
701 QGPSVTDLEMPHYSTFAYFPTEVTPHAFTPSSRQQDLVSTVNVVYSQTTQPVYNGETPLQPSYSSEVFPLVTPLLLDNQILNTTPAASSSDSALHATPVF
801 PSVDVSFESILSSYDGAPLLPFSSASFSSELFRHLHTVSQILPQVTSATESDKVPLHASLPVAGGDLLLEPSLAQYSDVLSTTHAASETLEFGSESGVLY
901 KTLMFSQVEPPSSDAMMHARSSGPEPSYALSDNEGSQHIFTVSYSSAIPVHDSVGVTYQGSLFSGPSHIPIPKSSLITPTASLLGDGEWSGAS
1001 SDSEFLLPDTDGLTALNISSPVSVAEFTYTTSVFGDDNKALSKSEIIYGNETELQIPSFNEMVYPSESTVMPNMYDNVNKLNASLQETSVSISSTKGMFP
1101 GSLAHTTTKVFDHEISQVPENNFSVQPTHTVSQASGDTSLKPVLSANSEPASSDPASSEMLSPSTQLLFYETSASFSTEVLLQPSFQASDVDTLLKTVLP
```

FIG. 1A

```
1201  AVPSDPILVETPKVDKISSTMLHLIVSNSASSENMLHSTSVPVFDVSPTSHMHSASLQGLTISYASEKYEPVLLKSESSHQVVPSLYSNDELFQTANLEI
1301  NQAHPPKGRHVFATPVLSIDEPLNTLINKLIHSDEILTSTKSSVTGKVFAGIPTVASDTFVSTDHSVPIGNGHVAITAVSPHRDGSVTSTKLLFPSKATS
1401  ELSHSAKSDAGLVGGGEDGDTDDGDDDDRDSDGLSIHKCMSCSSYRESQEKVMNDSDTHENSLMDQNNPISYSLSENSEEDNRVTSVSSDSQTGMDRS
1501  PGKSPSANGLSQKHNDGKEENDIQTGSALLPLSPESKAWAVLTSDEESGSGQGTSDSLNENETSTDFSFADTNEKDADGILAAGDSEITPGFPQSPTSSV
1601  TSENSEVFHVSEAEASNSSHESRIGLAEGLESEKKAVIPLVIVSALTFICLVVLVGILIYWRKCFQTAHFYLEDSTSPRVISTPPTPIFPISDDVGAIPI
1701  KHFPKHVADLHASSGFTEEFEEVQSCTVDLGITADSSNHPDNKHKNRYINIVAYDHSRVKLAQLAEKDGKLTDYINANYVDGYNRPKAYIAAQGPLKSTA
1801  EDFWRMIWEHNVEVIVMITNLVEKGRRKCDQYWPADGSEEYGNFLVTQKSVQVLAYYTVRNFTLRNTKIKKGSQKGRPSGRVVTQYHYTQWPDMGVPEYS
1901  LPVLTFVRKAAYAKRHAVGPVVVHCSAGVGRTGTYIVLDSMLQQIQHEGTVNIFGFLKHIRSQRNYLVQTEEQYVFIHDTLVEAILSKETEVLDSHIHAY
2001  VNALLIPGPAGKTKLEKQFQLLSQSNIQQSDYSAALKQQNREKNRTSSIIPVERSRVGISSLSGEGTDYINASYIMGYYQSNEFIITQHPLLHTIKDFWR
2101  MIWDHNAQLVVMIPDGQNMAEDEFVYWPNKDEPINCESFKVTLMAEEHKCLSNEEKLIIQDFILEATQDDYVLEVRHFQCPKWPNPDSPISKTFELISVI
2201  KEEAANRDGPMIVHDEHGGVTAGTFCALTTLMHQLEKENSVDVYQVAKMINLMRPGVFADIEQYQFLYKVILSLVSTRQEENPSTSLDSNGAALPDGNIA
2301  ESLESLV*
```

FIG. 1B

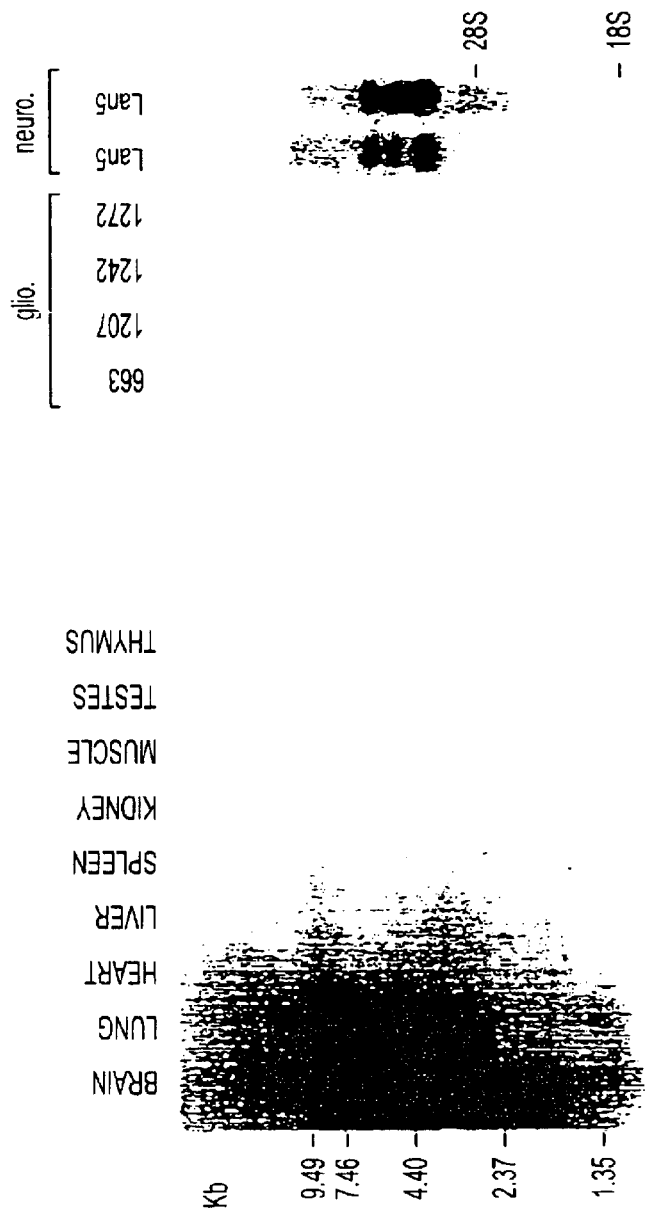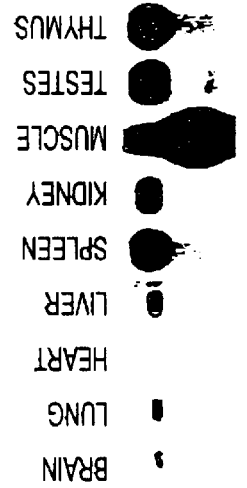

```
                1                                              50
                                 ↓
RPTP Beta   VEEIGWSYTGALNQK.NWGKKYPTCNSP.....KQSPINIDEDLTQVNVN
RPTP Gamma  .GDPYWAYSGAYGPE.HWVTSSVSCGGR.....HQSPIDILDQYARVGEE
CAH I       .ASPDWGYDDKNGPE.QWSKLYPIANGN.....NQSPVDIKTSETKHDTS
CAH II      ..SHHWGYGKHNGPE.HWHKDFPIAKGE.....RQSPVDIDTHTAKYDPS
CAH III     ..AKEWGYASHNGPD.HWHELFPNAKGE.....NQSPIELHTKDIRHDPS
CAH IV      .AESHWCYEVQAESS.NYPCLVPVKWGGNCQKDRQSPINIVTTKAKVDKK
CAH VI      QHVSDWTYSEGALDEAHWPQHYPACGGQ.....RQSPINLQRTKVRYNPS
CAH VII     .GHHGWGYGQDDGPASHWHKLYPIAQGD.....RQSPINIISSQAVYSPS CONSENSUS   .....WgY.g.ngpe.hwhklypia.ge.....rQSPinidt.ka..dps 51                                            100

RPTP Beta   LKKLKFQGWDKTSLENTFIHNTGKTVEINLTNDY...RVSGGVSEMVFKA
RPTP Gamma  YQELQLDGFDNESSNKTWMKNTGKTVAILLKDDY...FVSGAGLPGRFKA
CAH I       LKPISVS.YNPATA..KEIINVGHSFHVNFEDNDNRSVLKGGPFSDSYRL
CAH II      LKPLSVS.YDQATS..LRILNNGHAFNVEFDDSQDKAVLKGGPLDGTYRL
CAH III     LQPWSVS.YDGGSA..KTILNNGKTCRVVFDDTYDRSMLRGGPLPGPYRL
CAH IV      LGRFFSGYDKKQT..WTVQNNGHSVMMLLEN..KASISGG.LPAPYQA
CAH VI      LKGILNMTGYETQAG.EFPMVNNGHTVQIGLPSTMRMTVADG....IVYIA
CAH VII     LQPLELS.YEACMS..LSITNNGHSVQVDFNDSDDRTVVTGGPLEGPYRL CONSENSUS   lkplsvs.ydkass...tilNnGhtvqv...d.ydrsv..Ggplpgpyr.

101                                           150
                      ↓                           ↓
RPTP Beta   SKITFHWGKCNMSSDGSEHSLEGQKFPLEMQIYCFDADR.FSSFEEAVKG
RPTP Gamma  EKVEFHWG.HSNGSAGSEHSINGRRFPVEMQIFFYNPDD.FDSFQTAISE
CAH I       FQFHFHWG..STNEHGSEHTVDGVKYSAELHVAHWNSA.KYSSLAEAASK
CAH II      IQFHFHWG..SLDGQGSEHTVDKKKYAAELHLVHWNT..KYGDFGKAVQQ
CAH III     RQFHLHWG..SSDDHGSEHTVDGVKYAAELHLVHWNP..KYNTFKEALKQ
CAH IV      KQLHLHWS..DLPYKGSEHSLDGEHFAMEMHIVHEKEKGTSRNVKEAQDP
CAH VI      QQMHFHWGGASSEISGSEHTVDGIRHVIEIHIVHYNS..KYKTYDIAQDA
CAH VII     KQFHFHWG..KKHDVGSEHTVDGKSFPSELHLVHWNAK.KYSTFGEAASA CONSENSUS   kqfhfHWg...s.d.hGSEHtvdg.kf.aElhivhwn...kys.f.eA.s.
```

FIG. 7A-1

```
            151                                                            200
RPTP Beta   KGKLRALSILFEVGT.EENLDFKAIIDGVESVSRFGKQAALDPFILLNLL
RPTP Gamma  NRIIGAMAIFFQVSP.RDNSALDPIIHGLKGVVHHEKETFLDPFVLRDLL
CAH I       ADGLAVIGVLMKVG..EANPKLQKVLDALQAIKTKGKRAPFTNFDPSTLL
CAH II      PDGLAVLGIFLKVG..SAKPGLQKVVDVLDSIKTKGKSADFTNFDPRGLL
CAH III     RDGIAVIGIFLKIG..HENGEFQIFLDALDKIKTKGKEAPFTKFDPSCLF
CAH IV      EDEIAVLAFLVEAG.TQVNEGFQPLVEALSNIPKPEMSTTMAESSLLDLL
CAH VI      PDGLAVLAAFVEVKNYPENTYYSNFISHLANIKYPGQRTTLTGLDVQDML
CAH VII     PDGLAVGVFLETGD...EHPSMNRLTDALYMVRFKGTKAQFSCFNPKCLL CONSENSUS   pdglavl.i...vg..eenpg.q..idald.iktkgk.a.ft.fdp.dll 201                                                            250
                                    ↓                        ↓
RPTP Beta   PNST..DKYYIYNGSLTSPPCTDTVDWIVFKDTVSISESQLAVFC.EVLT
RPTP Gamma  PASL..GSYYRYTGSLTTPPCSEIVEWIVFRRPVPISYHQLEAFY.SIFT
CAH I       PSSL...DFWTYPGSLTHPPLYESVTWIICKESISVSSEQLAQFR.SLLS
CAH II      PESL...DYWTYPGSLTTPPLLECVTWIVLKEPISVSSEQVLKFR.KLNF
CAH III     PACR...DYWTYQGSFTTPPCEECIVWLLLKEPMTVSSDQMAKLR.SLLS
CAH IV      PKEEKLRHYFRYLGSLTTPTCDEKVVWTIVFREPIQLHREQILAFSQKLYY
CAH VI      PRNL..QHYYTYHGSLTTPPCTENVHWEVLADFVKLSRTQVWKLENSLLD
CAH VII     PAS...RHYWTYPGSLTTPPLSESVTWIVLREPICISERQMGKF.RSLLF CONSENSUS   Pasl....ywtYpGSlTtPpc.e.vtWivlkepis.sseQlakfr.sll.

251                       283
RPTP Beta   MQQSGYVMLMDYLQNNFREQQYKFSRQVFSSYT
RPTP Gamma  TEQQDHVKSVEYLRNNFRPQQRLHDRVVSKSAV
CAH I       NVEGD..NAVPMQHNN.RPTQPLKGRTVRASF.
CAH II      NGEGE...PEELMVDNWRPAQPLKNRQIKASFK
CAH III     SAENE...PPVPLVSNWRPPQPINNRVVRASFK
CAH IV      DKEQT.....VSMKDNVRPLQQLGQRTVMIKSGA
CAH VI      HRNKT.......IHNDYRRTQPLNHRVVESNFP
CAH VII     TSEDD...ERIHMVNNFRPPQPLKGRVVKASFR CONSENSUS   ..e.d......y.vnnfRp.Qplk.Rvv.asfk
```

FIG. 7A-2

PERCENT SIMILARITY

| | RPTP Beta | RPTP Gamma | CAH I | CAH II | CAH III | CAH IV | CAH VI | CAH VII |
|---|---|---|---|---|---|---|---|---|
| RPTP Beta | 100.0 | | | | | | | |
| RPTP Gamma | 58.1 | 100.0 | | | | | | |
| CAH I | 50.4 | 48.1 | 100.0 | | | | | |
| CAH II | 49.0 | 51.7 | 73.0 | 100.0 | | | | |
| CAH III | 48.7 | 53.7 | 69.9 | 71.0 | 100.0 | | | |
| CAH IV | 44.8 | 48.0 | 44.6 | 48.7 | 48.6 | 100.0 | | |
| CAH VI | 46.6 | 45.0 | 48.1 | 51.7 | 53.7 | 47.7 | 100.0 | |
| CAH VII | 47.1 | 49.0 | 65.0 | 69.9 | 64.5 | 47.1 | 51.3 | 100.0 |

FIG. 7B 1   2

```
RPTPβ   31 KLVEEIGWSYTGALNQKNWGKKYPTCNSPKQSPINIDEDLTQVNVNLKKL 80
           |||||:||||||||||||||||||||.|||||||||||||||||||||||
3F8      1 KLVEEMGWSYTGALNQKNWGKKYPICNSPKQSPINIDEDLTQVNVNLKKL 50

81 KFQGWDKTSLENTFIHNTGKTVEINLTNDYRVSGGVSEMVFKASKITFHW 130
           |||||:|.|||||||||||||||||||||||  :|||:||.||||||:||||
        51 KFQGWEKPSLENTFIHNTGKTVEINLTNDYYLSGGLSEKVFKASKMTFHW 100

131 GKCNMSSDGSEHSLEGQKFPLEMQIYCFDADRFSSFEEAVKGKGKLRALS 180
           ||||:||:|||||||||||||||||:|||||||||||.|||||:|||||
       101 GKCNVSSEGSEHSLEGQKFPLEMQVYCFDADRFSSFEETVKGKGRLRALS 150

181 ILFEVGTEENLDFKAIIDGVESVSRFGKQAALDPFILLNLLPNSTDKYYI 230
           ||||:|.|||||:|||||.|||||||||||||||||  |||||||||||
       151 ILFEIGVEENLDYKAIIDGTESVSRFGKQAALDPFILQNLLPNSTDKYYI 200

231 YNGSLTSPPCTDTVDWIVFKDTVSISESQLAVFCEVLTMQQSGYVMLMDY 280
           |||||||||||||:||||||||||||||:||||||||||||||||||||
       201 YNGSLTSPPCTDTVEWIVFKDTVSISESQLPVFCEVLTMQQSGYVMLMDY 250

281 LQNNFREQQY 290
           ||||||||||
       251 LQNNFREQQY 260
```

FIG. 14

RPTP-β ANTIBODIES

This application is a continuation of U.S. Ser. No. 09/644,293 filed Aug. 23, 2000, now abandoned, which is a divisional of U.S. Ser. No. 08/081,929, filed Jun. 23, 1993 (U.S. Pat. No. 6,160,090), which is a continuation-in-part of U.S. Ser. No. 07/961,235, filed Oct. 15, 1992, now abandoned and a continuation-in-part of U.S. Ser. No. 08/015,973, filed Feb. 10, 1993, now U.S. Pat. No. 5,604,094, which is a continuation-in-part of U.S. Ser. No. 07/654,188, filed Feb. 26, 1991, now abandoned.

1. INTRODUCTION

The present invention relates to a new class of receptor protein tyrosine phosphatase molecule, the ligands that bind this new class of receptor, and the uses of such receptors and ligands. Specifically, the members of this new class of receptor protein tyrosine phosphatase molecule are proteoglycans and/or possess an extracellular carbonic anhydrase structural domain. The characterization of one member of this new class, RPTPβ, is described in the working examples presented herein. As is further demonstrated in the Working Examples presented below, the ligands which bind the receptor protein tyrosine phosphatases of the invention may be, for example, tenascin and/or members of the cell adhesion molecule (CAM) family of extracellular molecules.

2. BACKGROUND OF THE INVENTION

2.1 Protein Phosphorylation and Signal Transduction

Cells rely, to a great extent, on extracellular molecules as a means by which to receive stimuli from their immediate environment. These extracellular signals are essential for the correct regulation of such diverse cellular processes as differentiation, contractility, secretion, cell division, cell migration, contact inhibition, and metabolism. The extracellular molecules, which can include, for example, hormones, growth factors, or neurotransmitters, act as ligands that bind specific cell surface receptors. The binding of these ligands to their receptors triggers a cascade of reactions that brings about both the amplification of the original stimulus and the coordinate regulation of the separate cellular processes mentioned above.

A central feature of this process, referred to as signal transduction (for recent reviews, see Posada, J. and Cooper, J. A., 1992, Mol. Biol. Cell 3:583–592; Hardie, D. G., 1990, Symp. Soc. Exp. Biol. 44:241–255), is the reversible phosphorylation of certain proteins. The phosphorylation or dephosphorylation of amino acid residues triggers conformational changes in regulated proteins that alter their biological properties. Proteins are phosphorylated by-protein kinases and are dephosphorylated by protein phosphatases. Protein kinases and phosphatases are classified according to the amino acid residues they act on, with one class being serine-threonine kinases and phosphatases (reviewed in Scott, J. D. and Soderling, T. R., 1992, 2:289–295), which act on serine and threonine residues, and the other class being the tyrosine kinases and phosphatases (reviewed in Fischer, E. H. et al., 1991 Science 253:401–406; Schlessinger, J. and Ullrich, A., 1992, Neuron 9:383–391; Ullrich, A. and Schlessinger, J., 1990, Cell 61:203–212), which act on tyrosine residues. The protein kinases and phosphatases may be further defined as being receptors, i.e., the enzymes are an integral part of a transmembrane, ligand-binding molecule, or as non-receptors, meaning they respond to an extracellular molecule indirectly by being acted upon by a ligand-bound receptor. Phosphorylation is a dynamic process involving competing phosphorylation and dephosphorylation reactions, and the level of phosphorylation at any given instant reflects the relative activities, at that instant, of the protein kinases and phosphatases that catalyze these reactions.

While the majority of protein phosphorylation occurs at serine and threonine amino acid residues, phosphorylation at tyrosine residues also occurs, and has begun to attract a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Cantley, L. C. et al., 1991, Cell 64:281–302; Hunter T., 1991, Cell 64:249–270; Nurse, 1990, Nature 344:503–508; Schlessinger, J. and Ullrich, A., 1992, Neuron 9:383–391; Ullrich, A. and Schlessinger, J., 1990, Cell 61:203–212). Subversion of normal growth control pathways leading to oncogenesis has been shown to be caused by activation or overexpression of tyrosine kinases which constitute a large group of dominant oncogenic proteins (reviewed in Hunter, T., 1991, Cell 64:249–270).

In addition, since the initial purification, sequencing and cloning of a protein tyrosine phosphatase (Thomas, M. L. et al., 1985, Cell 41:83), additional potential protein tyrosine phosphatases have been identified at a rapid pace. (See, for example, Kaplan, R. et al., 1990, Proc. Natl. Acad. Sci. USA 87:7000–7004; Krueger, N. X. et al., 1990, EMBO J. 9:3241–3252; Sap, J. et al., 1990, Proc. Natl. Acad. Sci. USA 87:6112–6116). Because the number of different protein tyrosine phosphatases that have been identified is increasing steadily, speculation has arisen that the protein tyrosine phosphatase family may be as large as the protein tyrosine kinase family (Hunter, T., 1989, Cell 58:1013–1016). With this increase in the reported cloning of protein tyrosine phosphatase genes, the role that the regulation of dephosphorylation may have in the control of cellular processes has also begun to receive more attention.

2.2 Protein Tyrosine Phosphatases

As mentioned above, protein tyrosine phosphatases (PTPases) can be classified into two subgroups, the non-receptor and receptor classes. The non-receptor class is composed of low molecular weight, cytosolic, soluble proteins. All known non-receptor PTPases contain a single conserved catalytic phosphatase domain of approximately 230 amino acid residues. (See, for example, Charbonneau et al., 1989, Proc. Natl. Acad. Sci. USA 86:5252–5256; Cool et al., 1989, Proc. Natl. Acad. Sci. USA 86:5257–5261; Guan et al., 1990, Proc. Natl. Acad. Sci. USA 87:1501–1502; Lombroso et al., 1991, Proc. Natl. Acad. Sci. USA 88:7242–7246.) Sequence analysis reveals that about 40 of the amino acids of the catalytic domain are highly conserved, and a very highly conserved segment of 11 amino acid residues with the consensus sequence [I/V]HCXAGXXR[S/T]G, is now recognized to be a hallmark of the protein tyrosine phosphatase catalytic domain.

The receptor class is made up of high molecular weight, receptor-linked PTPases, termed RPTPases. Structurally resembling growth factor receptors, RPTPases consist of an extracellular, putative ligand-binding domain, a single transmembrane segment, and an intracellular catalytic domain (reviewed in Fischer et al., 1991, Science 253:401–406).

The intracellular segments of almost all RPTPases are very similar. These intracellular segments consist of two catalytic phosphatase domains of the type described above, separated by an approximately 58 amino acid residue segment. This two domain motif is usually located approximately 78 to 95 amino acid residues from the transmembrane segment and is followed by a relatively short carboxy-terminal amino acid sequence. The only known exception is the isoform HPTPβ (Krueger, N. X. et al., 1990, EMBO J. 9:3241), which contains only one catalytic phosphatase domain.

While the intracellular RPTPase segments are remarkably highly conserved, the RPTPase extracellular domains are highly divergent. For example, certain RPTPases possess a heavily glycosylated external domain and a conserved cysteine-rich region (Thomas, M. L. et al., 1985, Cell 41:83; Thomas, M. L. et al., 1987, Proc. Natl. Acad. Sci. USA 84:5360; Ralph, S. J. et al., 1987, EMBO J. 6:1251–1257) while others contain immunoglobulin G-like (Ig) domains linked to fibronectin type III repeats (Streuli, M. et al., 1989, Proc. Natl. Acad. Sci. USA 86:8698; Streuli, M. et al., 1988, J. Exp. Med. 168:1523). Still other RPTPases contains only multiple fibronectin type III repeats (Krueger, N. X. et al., 1990, EMBO J. 9:3241), while certain RPTPases have smaller external domains that contain several potential glycosylation sites (Jirik, F. R. et al., 1990, FEBS Lett. 273:239). The ligands that regulate RPTPs have not been identified. It has been speculated that circulating extracellular factors are unlikely to bind to those receptors containing Ig and/or fibronectin Type III repeats and that interaction with other surface antigens, perhaps on other cells, is more likely to be the case with these receptors.

Because enhanced tyrosine phosphorylation has been shown to be responsible for causing cellular transformation, underexpression, or inactivation, of protein tyrosine phosphatases may also potentially result in oncogenesis. For this reason, tyrosine-specific phosphatase genes are candidate recessive oncogenes or tumor suppressor genes. In support of this theory, the human RPTPase, RPTPγ, has been shown to map to a chromosomal region, 3p14–21, which is frequently deleted in renal cell and lung carcinomas (LaForgia, S. et al., 1991, Proc. Natl. Acad. Sci. USA 88:5036–5040). Recent studies, however, indicate that protein tyrosine phosphatase action need not only be suppressive. It has been shown that members of the src family of non-receptor tyrosine kinases contain inhibitory tyrosine phosphorylation sites in the carboxy terminal tails (reviewed by Hunter, T., 1987, Cell 49:1–14). When these sites are phosphorylated, the molecules' tyrosine kinase activity is inhibited (Nada, S. et al., 1991, Nature 351:69–72). It has further been demonstrated that, in T cells, the dephosphorylation of such inhibitory sites by a protein tyrosine phosphatase (CD45) leads to enhanced tyrosine phosphorylation (Ledbetter, J. A. et al., 1989, Proc. Natl. Acad. Sci. USA 86:8628–8632), indicating, therefore, that phosphatases may function as activating and well as inhibitory signaling enzymes. Also, dephosphorylation of a tyrosine residue has been suggested to be an obligatory step in the mitotic activation of the maturation-promoting factor kinase (Morla, A. O. et al., 1989, Cell 58:193–203). Taken together, the above observations suggest that PTPases may play an important role in cellular control mechanisms, as effectors in mechanisms of transmembrane signaling, as cell-cycle regulators, and as potential oncogenes and anti-oncogenes.

3. SUMMARY OF THE INVENTION

The present invention relates to a new class of receptor protein tyrosine phosphatase molecule, to the family of ligands that binds this new class of receptor, and to the uses of such receptors and ligands. Specifically, the members of this new class of receptor protein tyrosine phosphatase molecule are proteoglycans and/or possess an extracellular carbonic anhydrase structural domain. The characterization of one such receptor molecule, RPTPβ, is described in the working examples presented herein.

The ligands which bind the receptor protein tyrosine phosphatases of the invention may include, but are not limited to, tenascin and/or members of the cell adhesion molecule (CAM) family of extracellular molecules. The discovery that CAMs bind receptor protein tyrosine phosphatases represents the first identification of a natural ligand for this type of receptor. Binding of two CAMs, namely N-CAM and Ng-CAM, to the receptor protein tyrosine phosphatases of the invention is demonstrated in the working examples presented herein. In addition, as is demonstrated in the Working Example presented below in Section 8, the receptor protein tyrosine phosphatases of the invention also bind the extracellular matrix molecule tenascin. The receptors and the receptor-binding ligands of the invention may be used to develop compounds and strategies for modulating cellular processes under the control of the receptor protein tyrosine phosphatases. Such processes include, but are not limited to, normal cellular functions such as differentiation, metabolism, cell cycle control, wound healing and neuronal function; cellular behavior such as motility, migration, and contact inhibition, in addition to abnormal or potentially deleterious processes such as virus-receptor interactions, inflammation, cellular transformation to a cancerous state, and the development of Type 2, insulin Independent, diabetes mellitus. Compounds that may interfere with ligand binding are described and methods for identifying other potential ligands, such as CAM-type ligands, growth factors, or extracellular matrix components, are discussed.

4. BRIEF DESCRIPTION OF THE FIGURES

FIG. 1. The amino acid sequence of RPTPβ [SEQ ID NO:2]. The protein sequence of RPTPβ containing 2308 amino acids is indicated. The hydrophobic signal peptide is underlined (amino acids 1–21), and the transmembrane peptide is designated in bold-type (amino acids 1637–1662). The 21 potential N-glycosylation sites are indicated by the arrows. The CAH-related domain and FIG. 2(A–B). Chromosomal localization of human RPTPβ. A. Presence of the RPTPβ gene in a panel of 17 rodent-human hybrids. A completely stippled box indicates that the hybrid named in the left column contains the chromosome indicated in the upper row; lower-right stippling indicates presence of the long arm (or part of the long arm, indicated by a smaller fraction of stippling) of the chromosome shown above the column; upper left stippling indicates presence of the short arm (or partial short arm) of the chromosome listed above the column; an open box indicates absence of the chromosome above the column; the column for chromosome 7 is boldly outlined and stippled to highlight correlation of presence of this chromosome with the presence of the RPTPβ gene. The pattern of retention of the RPTPβ sequences in the hybrids is shown to the right where presence of the gene in the hybrids is indicated by a stippled box with a plus sign and absence of the gene is indicated by an open box enclosing a minus sign. B. RPTPβ maps to 7q31–q33. Chromosome in situ hybridization of a 1.8 kb RPTPβ cDNA to normal human metaphases confirmed localization of the gene to 7q and revealed a peak of grains centered over region 7q31.3–7q32 as illustrated on the right to the chromosome sketch. Each dot representing an autoradiographic grain.

FIG. 3(A–C). Analysis of the expression of RPTPβ in various murine tissues and cell lines. A. Poly A+RNA (1 μg per sample) from the various murine tissues indicated were loaded onto a 1.0% agarose/2.2 M formaldehyde gel and probed with the per amplified murine DNA fragment, pBSMBDII (described in Materials and Methods, Section 6.1.4). B. The blot in A. was stripped of probe and rehybridized with a $^{32}$p labeled rat actin probe. C. 20 μg of total cellular RNA (lanes 1–5) and 1 μg of Poly A+RNA (lane 6) isolated from the various glioblastoma and neuroblastoma cell lines indicated were loaded onto on RNA gel and probed with a DNA fragment isolated from the human brain stem cDNA clone that begins with sequences just 5' of the transmembrane region and extends and includes all of the sequences in phosphatase domain I.

FIG. 4(A–B). Northern blots to identify alternative splicing of RPTPβ transcripts. A. A schematic diagram of the protein encoded by the full length RPTPβ cDNA compared to the putative protein encoded by the two independently isolated cDNA clones that carry an identical deletion of 258 bp in the extracellular region of the protein. The position of the deletion is indicated by the dotted line with the number of the amino acid that remains at both the 5' and 3' end of the deletion indicted. The location of the two probes used in Northern analysis (probes 1 and 2) are indicated. TM, transmembrane peptide; DI, phosphatase domain I and DII, phosphatase domain II. B. Poly A+RNA (1 μg) isolated from the Lan 5 neuroblastoma cell line was separated on a RNA formaldehyde gel and probed with human probe 1 (P1) that contains 1.3 kb of sequences derived from the extreme 5' end of the cDNA clone and human probe 2 (P2) that contains 1.6 kb of sequences derived from the portion of the full length cDNA clone that is deleted in clones BS-d14 and Caud11.

Figure 5A:

FIG. 5(A–B). In situ hybridization analysis of RPTPβ in developing and adult mouse brain. A. A sagittal section through an embryonic day 20 (E20) mouse shows that RPTPβ is preferentially expressed in the developing central nervous system. The highest level of expression is seen in the ventricular zone (VZ). B. A sagittal section through the adult mouse brain shows discrete bands of expression in the Purkinje cell of the cerebellum, the dentate gyrus (OG), and the anterior horn of the lateral ventricle (AH).

Figure 6:
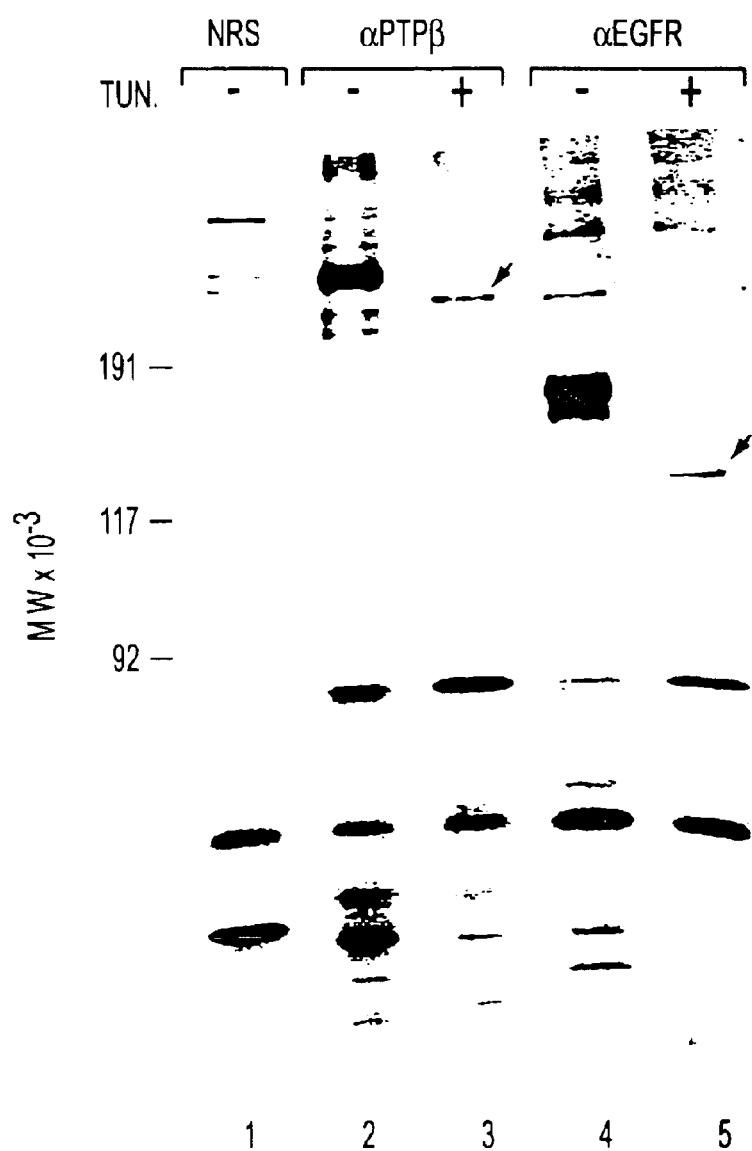

FIG. 6. Identification of endogenous RPTPβ protein expression in Lan 5 cells. Immunoprecipitation of RPTPβ with normal rabbit serum (NRS, lane 1) and immune RPTPβ antiserum (αPTPβ, lanes 2 and 3) from lysates of $^{35}$S methionine-labeled Lan 5 cells that had been labeled in the absence (lanes 1 and 2) or presence of tunicamycin (lane 3). Apparent molecular weight is approximately 300 kD in the absence, and 250 kD is the presence, of tunicamycin. Immunoprecipitation of the EGF receptor with RK2 antibody (λaEGFR, lanes 4 and 5) from lysates of $^{35}$S methionine-labeled Lan 5 cells labeled in the absence (lane 4) and presence (lane 5) of tunicamycin.

FIG. 7. Identification of a CAH-related domain in the extracellular region of RPTPβ. A. The alignment of the amino acid sequence of the CAH-related domain of RPTPβ with the corresponding domain of RPTPε and the six different isoforms of CAH [SEQ ID NOS:4–9] (Deutsch, H. F., 1987, Int. J. Biochem. 19:101–113). The amino acid sequences that are boxed in black are those that are identical in all six isoforms of CAH. The sequences that are boxed in the gray hatches are those that are identical between the CAH-related domains of RPTPβ and RPTPγ. B. The percent similarity, taking into account conservative substitutions of amino acids utilizing the program, between the CAH-related domains of RPTPβ and RPTPγ and the six isoforms of CAH is indicted in this grid.

Figure 8:

FIG. 8 Polyacrylamide gel of an immunoprecipitation, using $^{35}$S-NaSO$_4$-labeled cell lysates from 293 cells transfected with RPTPβ cDNA (Lane 1) or from control, 293 cells transfected with vector alone (Lane 2). Antiserum used was directed against RPTPβ, as described in Section 6.1.5.

Figure 9:
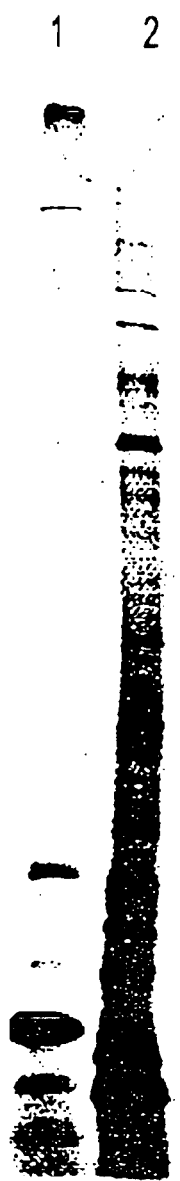

FIG. 9 Polyacrylamide gel of an immunoprecipitation, using $^{35}$S-Met-labeled cell lysates from 293 cells transfected with RPTPβ cDNA (Lane 1) or from control, 293 cells transfected with vector alone (Lane 2). Antiserum used was directed against RPTPβ, as described in Section 6.1.5.

Figure 10:

FIG. 10 Polyacrylamide gel of an immunoprecipitation, using $^{35}$S-Met-labeled cell lysates from 293 cells transfected with RPTPβ DNA (Lanes 3 and 4) or from control, 293 cells transfected with vector alone (Lane 1 and 2). Lanes 2 and 4 represent lysates that have been chondroitinase ABC-treated, while 1 and 3 are untreated lysates. Antiserum used was directed against RPTPβ, as described in Section 6.1.5.

Figure 11B:
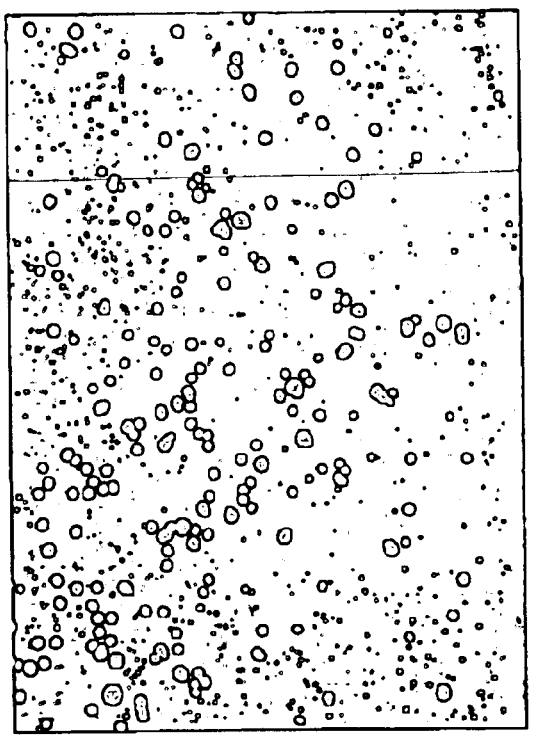
Figure 11A:

FIG. 11(A–B). Effects of the proteoglycan 3F8 on aggregation of Ng-CAM-Covaspheres. Green-fluorescing Ng-CAM-Covaspheres after incubation for 2 hours at 25° (A) in the presence of 10 μg/ml of BSA. (B) 30 μg/ml 3F8 proteoglycan. Covaspheres were visualized using a Nikon Diaphot microscope equipped for fluorescence and were photographed using a N2000 camera.

Figure 12:
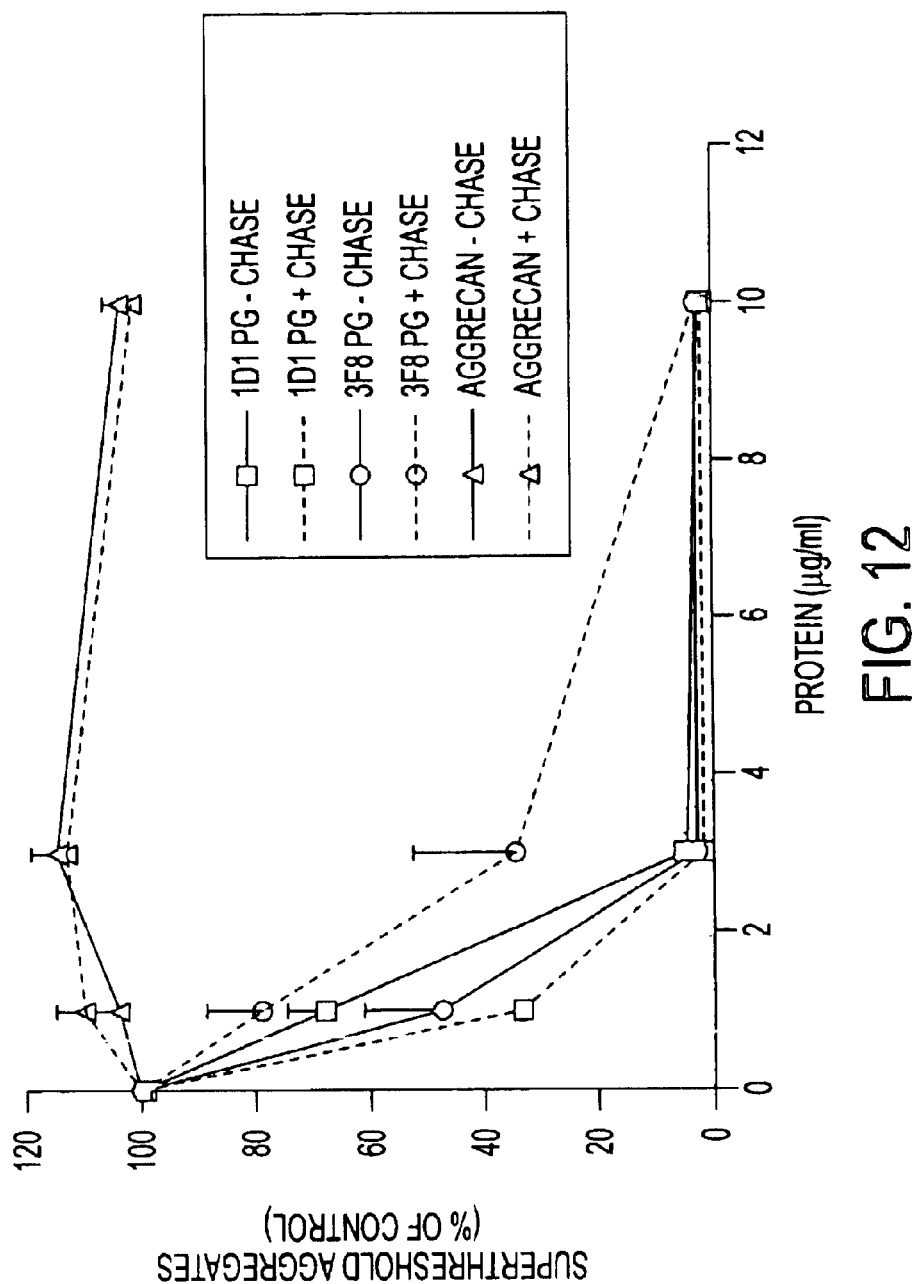

FIG. 12. Inhibition of NG-CAM-Covasphere aggregation by 3F8. The appearance of superthreshold aggregates of Covaspheres coated with Ng-CAM was measured after 2 hours using a Coulter counter. 6 μl samples of Ng-Covaspheres were mixed in a final volume of 60 μl PBS in the presence of various concentrations of native 3F8 proteoglycan (PG, solid lines) and chondroitinase-treated 3F8 proteoglycan core (Chase, dashed lines) from 7-day brain. Data represent means (N=3) ± the standard error of the % of the control levels of superthreshold aggregates detected. The mean level of superthreshold particles in control samples was 32,582±788.

Figure 13:
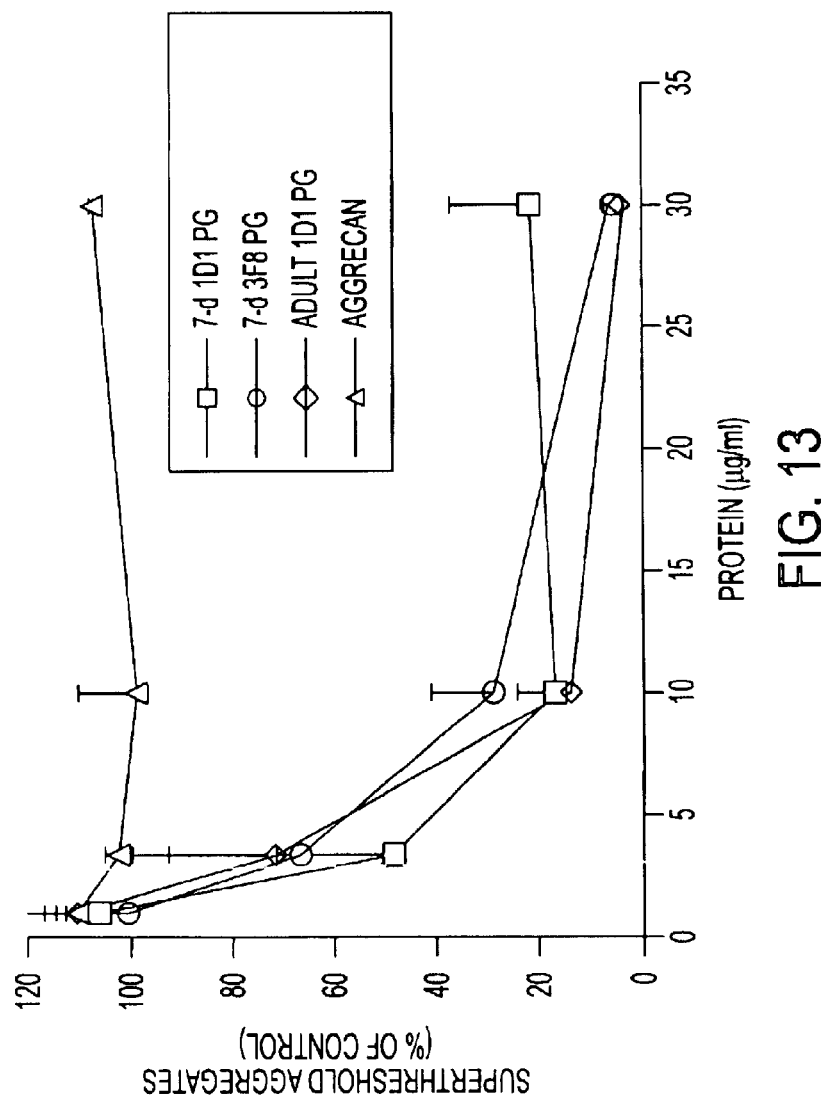
Figure 15A:
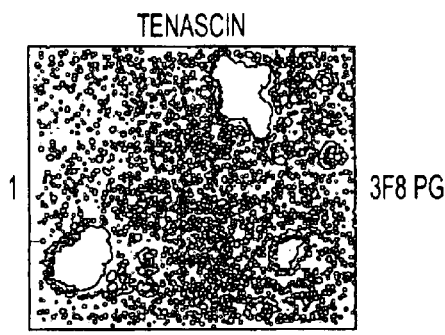
Figure 15B:
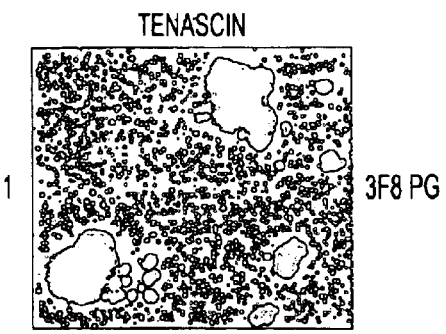
Figure 15C:
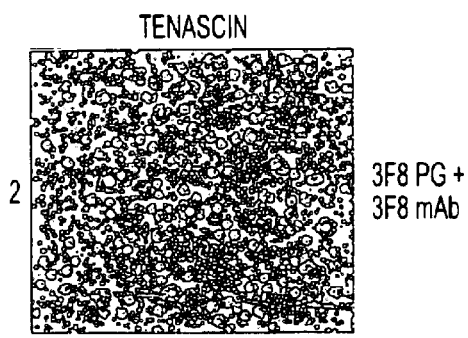
Figure 15D:
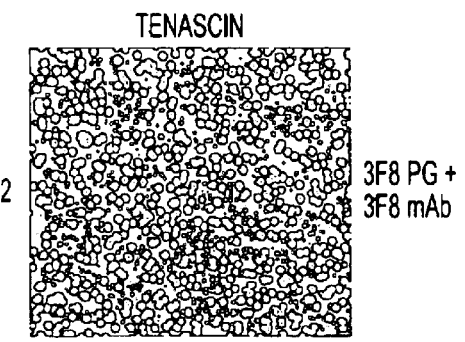
Figure 15E:
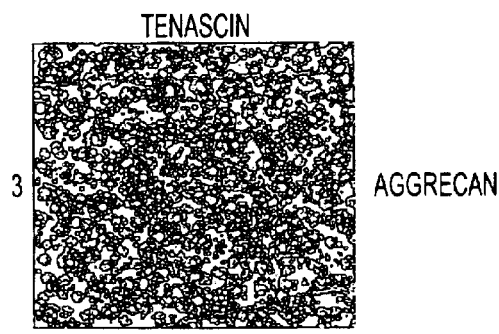
Figure 15F:
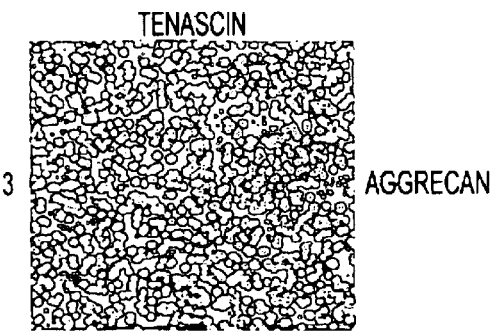
Figure 15G:
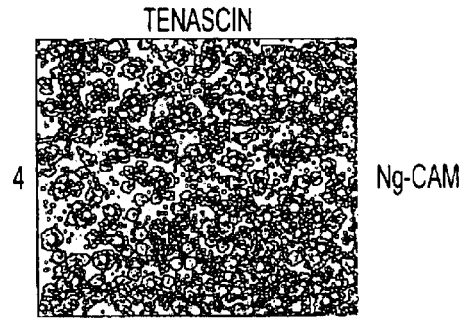
Figure 15H:
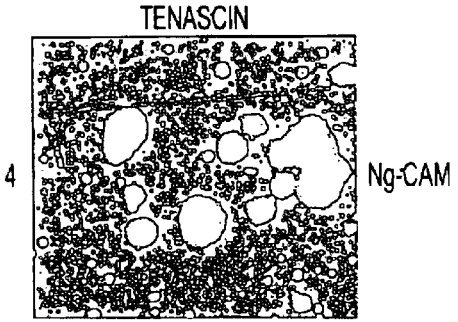

FIG. 13. Inhibition of N-CAM-Covasphere aggregation by chondroitinase-treated 3F8 (circles). The appearance of superthreshold aggregates of Covaspheres coated with N-CAM was measured after 2 hours. Chondroitinase-treated 3F8 used. Data represents a mean (N=3) of the % control levels of superaggregates detected. The mean level of superthreshold particles in control samples was 19,993+/−2,190.

FIG. 14. Comparison of the amino acid sequences of the carbonic anhydrase domains contained in rat 3F8 [SEQ ID NO:10] and human RPTPβ proteins. Top sequence represents the RPTPβ sequence, bottom line the 3F8 sequence.

FIG. 15(A–H). Binding of tenascin to 3F8 proteoglycan (PG). Panels (1–4) consist of identical fields which were visualized specifically for green-fluorescing Covaspheres (right) and red-fluorescing (left) tenascin Covaspheres. Panel 1: tenascin Covaspheres mixed with green-fluorescing 3F8 PG Covaspheres; Panel 2: tenascin Covaspheres mixed with green-fluorescing 3F8 PG Covaspheres in the presence of 3F8 monoclonal antibodies; Panel 3: tenascin Covaspheres mixed with green-fluorescing aggegrecan Covaspheres; Panel 4: tenascin Covaspheres mixed with green fluorescing Ng-CAM Covaspheres.

5. DETAILED DESCRIPTION OF THE INVENTION

This invention involves a new class of receptor protein tyrosine phosphatase molecule whose members are proteoglycans and/or possess an extracellular carbonic anhydrase structural domain. In addition, two classes of molecules, first, the extracellular matrix molecule tenascin, and second, the cell adhesion family of molecules (CAMs), that bind to, and act as ligands for, this new class of receptor are also described. The discovery that CAMs bind receptor protein tyrosine phosphatases represents the first identification of a natural ligand for this type of receptor. Binding of two CAMs, namely N-CAM and-Ng-CAM, to the receptor protein tyrosine phosphatases of the invention is demonstrated in the working examples presented herein. The further discovery that the extracellular matrix molecule tenascin binds the receptor protein tyrosine phosphatases of the invention identifies the second natural ligand for these receptors.

A number of uses for the receptors and the receptor-binding ligands of the invention are also encompassed in the invention. Briefly, the receptor and the receptor-binding ligands may be used to develop compounds and strategies for modulating cellular processes under the control of the receptor protein tyrosine phosphatases. Such processes include, but are not limited to, normal cellular functions such as differentiation, metabolism, cell cycle control, wound healing, and neuronal function; cellular behaviors such as motility, migration, contact inhibition, and signal transduction; in addition to abnormal or potentially deleterious processes such as virus-receptor interactions, inflammation, cellular transformation to a cancerous state, and the development of Type 2, insulin independent diabetes mellitus. Compounds that may interfere with ligand binding are described and methods for identifying other potential ligands, such as CAM-type ligands, growth factors, or extracellular matrix components, are discussed. Finally, working examples are presented in which one member of the new RPTPase family of molecules, RPTPβ, is characterized, and additionally two members of the CAM family, N-CAM and Ng-CAM, and the extracellular matrix molecule tenascin are all shown to bind to the new RPTPase class of receptor.

5.1 RPTPases

The RPTPases of the invention that are proteoglycans may be modified with macromolecules composed of glycosaminoglycan (GAG) chains (glycans) covalently bound to the RPTPase protein core. GAG components may consist of such units as hexosamine (D-glucosamine (GlcN) or D-galactosamine (GalN)), and either hexuronic acid (HexA; D-glucuronic acid (GlcA) or L-iduronic acid (IdoA)) or galactose units (as in keratin sulfate) that are arranged in alternating, unbranched sequence, and carry sulfate substituents in various positions. The glycan backbones of the RPTPase molecules may include, but are not limited to, a basic structure composed of $(HexA-GalN)_n$, $(HexA-GlcN)_n$, or $(Gal-GlcN)_n$ disaccharide units. While these structures connote the basic structure of the RPTPase modifications, such modifications may also contain marked heterogeneity within as well as between the individual polysaccharide chains. Such heterogeneity is an expected byproduct of the mechanism of GAG biosynthesis, and may include, but is not limited to differences in sulfate substitutions along the chain and epimerization of one unit to another (GlcA to IdoA, for example). At least one glycan chain must be attached to the protein core of each proteoglycan RPTPase. Glycan chains may, but are not required to, be attached to the protein core at the serine (Ser) amino acid residue of the sequence, Ser-Gly-X-Gly, where Gly is a glycine amino acid residue and X is any amino acid residue. Additionally, glycan chains may be attached to the protein core at the serine residue in the sequence Z-Ser-Gly or Z-Gly-Ser, where Z is an acidic amino acid residue.

The members of the RPTPase class of the invention may include an extracellular stretch of amino acids that shares similarity with the known carbonic anhydrase isoforms (Deutsch, H. F., 1987, Int. J. Biochem. 19:101–113). Such sequences need not have carbonic anhydrase enzymatic activity. One or more complete or partial carbonic anhydrase motifs may be present on a single RPTPase molecule. Within the CAH region of similarity there may exist amino acid substitutions, as well as short amino acid deletions, and/or short amino acid additions that diverge from the known CAH isoforms. Such divergent sequences are acceptable as long as the overall amino acid sequence similarity to CAH remains at least about 25% and/or the tertiary structure or the domain remains similar to that of CAH.

Presented in the working example in Section 6 is the characterization of one member, RPTPβ, of this new class of RPTPase molecule. In this example, it is shown that RPTPβ not only contains a CAM-like domain but is also a proteoglycan.

5.2 RPTPase Ligands

One class of molecules that acts as a preferred ligand for the receptors of the invention is the cell adhesion family of molecules (CAMs). Such molecules include, but are not limited to, any member of the classes of $Ca^{2+}$-independent CAMs, cadherins, which are $Ca^{2+}$-dependent CAMs, and integrins, which are $Ca^{2+}$- or $Mg^{2+}$-dependent CAMs. $Ca^{2+}$-independent CAMs include such molecules as the N-CAM family, Ng-CAM, L1, J1, Fasciclin III, and MAG molecules. The cadherins include such molecules as N-cadherin, E-cadherin, P-cadherin, L-CAM, B-cadherin, and T-cadherin. As is demonstrated in the working example presented in Section 7, two members of the CAM family of molecules, N-CAM and Ng-CAM, bind members of the RPTPase class of molecule described in this invention.

It had previously been speculated that receptor phosphatases themselves may function as cell adhesion molecules because some of them contain motifs such as IgG-like or fibronectin Type III repeats typical of CAMs. In addition, because CAMs are known to undergo homotypic ("like" molecule) binding, it had been proposed that PTPases with IgG and fibronectin motifs may also under go homotypic interactions. It is of note, however, that IgG-like and fibronectin motifs are found in many surface receptors and proteins which do not undergo homotypic interactions. Contrary to this proposal, though the working Example of Section 6 described herein demonstrates that CAMs act as ligands for the RPTPase molecules of this invention, which contain no IgG-like motifs. Thus, even in the absence of peptide domain similarities, a ligand/receptor interaction does, in fact, occur between the RPTPase class of molecule disclosed in this invention and CAMs, where no interaction has previously been predicted to occur.

The ligands of the invention may be transmembrane proteins, glycosylphosphatidylinositol-linked membrane proteins, or secreted proteins. The molecules that constitute the ligands of this invention may contain one or more peptide domains, including, but not limited to, one or more Ig (immunoglobulin) domains (Williams, A. F., 1987, Immunol. Today 8:298–303), one or more fibronectin type III domains (Hynes, R. O., 1990, Fibronectins, Springer-Verlag, N.Y.), and/or one or more ectodomains (Takeichi, M., 1991, Science 251:1451–1455). Ig domains may share characteristics with both immunoglobulin constant and variable regions. Such characteristics may include pairs of cysteine residues, spaced approximately 60 amino acids apart, that form disulfide bonds with each other. Molecules may exhibit one or amino acid repeats of the sequence DRE, DXNDN, DXD, DVNE, DXE, and/or DPD. If the molecules are transmembrane proteins, such sequences should be present in the extracellular portion of the molecule.

Because the RPTPase molecules of this invention may be proteoglycans, several other non-CAM-like ligands may exist. For example, such extracellular matrix molecules as vitronectin, fibronectin, and laminin have been known to bind to the GAGs of certain proteoglycans. Also, growth factors, such as fibroblast growth factors, and Schwann cell growth factor, have also been demonstrated to have affinity for proteoglycan GAG chains. Therefore, molecules including, but not limited to extracellular matrix molecules and growth factors are potential ligands for the RPTPase class of molecule presented in this invention.

As is demonstrated in the Working Example presented below in Section 8, the extracellular matrix molecule tenascin acts as a ligand for the RPTPβ member of the RPTPase molecules of the invention. Therefore, the ligands of the invention may further be all or any part of the tenascin hexabrachion molecules that are capable of binding one or more of the members of the RPTPase molecules of the invention. Such tenascin molecules include molecules derived from human as well as other species, such as mouse, chicken and the like, and further include tenascin molecules comprising subunits encoded by any of the alternatively spliced tenascin mRNAs. The portions of the tenascin molecules which may act as ligands of the invention include, but are not limited to, any tenascin large subunit and/or any tenascin small subunit. Further, the tenascin molecules which act as ligands of the invention may include, but are not limited to, all or any portion of the terminal knob domain, the thick distal segment, and/or the thin proximal segment of any of the tenascin hexabrachion arms, all or any portion of a tenascin T-junction domain corresponding to the position wherein three tenascin hexabrachion arms join to form a trimer and/or all or any portion of a tenascin central knob, corresponding to the position wherein two tenascin trimers join to form a tenascin hexamer. Other portions of tenascin molecules which may act as ligands of the invention include all or any part of specific domains present as repeats (i.e., greater than one copy per hexabrachion arm) within the tenascin molecules. Such tenascin domain may include, but are not limited to, EGF-like domains, tenascin domains similar to Type-III domains of fibronectin, and/or tenascin carboxy-terminal domains similar to the carboxy-terminal region of fibrinogen β and γ chains, specifically that fibrinogen region which forms the globular domains of the fibrinogen D-module (Erickson, H. P. and Fowler, W. E., 1983, Ann. N.Y. Acad. Sci. 408: 146–163).

5.3 Uses and Administration of RPTPase Ligands

Depending on the individual molecule, some RPTPase molecules may become activated upon ligand binding, and others may become inactivated (the activity referred to here being the RPTPases' phosphatase activity). Ligand binding to RPTPase molecules may affect a variety of cellular processes. Such processes include, but are not limited to, normal cellular functions such as differentiation, metabolism, cell cycle control, wound healing, and neuronal function; cellular behavior, such as cell motility, migration, and contact inhibition; in addition to abnormal or potentially deleterious processes such as virus-receptor interactions, inflammation, cellular transformation to a cancerous state, and the development of Type 2, insulin independent diabetes mellitus. RPTPase/ligand binding may exert an effect on the above-mentioned processes within the RPTPase-exhibiting cell. In addition, because ligands of the invention, CAMs for example, are often cell surface proteins, RPTPase/ligand binding may elicit an effect on the ligand-exhibiting cell. Alternatively, RPTPases may contribute to the control of such cellular processes by exerting an effect directly on the ligand itself, via, for example, a ligand phosphorylation/dephosphorylation reaction. The receptors and the receptor-binding ligands of the invention may be used as drugs that can modulate the cellular processes under the control of the RPTPases. In addition, methods are presented below for the identification of compounds that affect RPTPase activity, and such compounds may also be used as drugs that can modulate one or more of the cellular processes mentioned above.

The receptors or their ligands may be used directly to modulate processes such as those mentioned above. For example, soluble RPTPases may be administered, using techniques well known to those skilled in the art, that could act to compete with endogenous transmembrane receptor molecules for available ligands, thus reducing or inhibiting ligand binding to endogenous RPTPases. The effect of such a procedure would be to activate, reduce or block the signal normally transduced into the cell (either the RPTPase-exhibiting cell, or the ligand-exhibiting cell) via ligand binding to transmembrane RPTPase. The RPTPases used here may include the entire molecule or, alternatively, only the RPTPase extracellular domain, or a part of the RPTPase extracellular domain thereof.

In addition, ligands may be administered, again, using techniques well known to those in the art. Such administration would lead to a greater than normal number of transmembrane RPTPases being bound by ligand, potentially causing an amplification of the ligand-bound state within cells exhibiting RPTPases. Alternatively, the administered ligand may be composed of a modified form of said ligand such that receptor binding may still occur, but the normal result of such binding (receptor activation or inactivation, as the case may be) does not occur. A ligand with such a design would act in much the same way that administration of soluble RPTPase would, in that both procedures would have the final effect of reducing the number of functionally bound RPTPase transmembrane molecules, therefore lowering or blocking the normal extracellular signal being transduced into the RPTPase-exhibiting cell via normal ligand binding to transmembrane RPTPase. The effect on a ligand-exhibiting cell, for example, one exhibiting cell surface CAMs, would also be the same in that an overall lower number of endogenous ligands would be bound, therefore lowering or blocking the effect of RPTPase binding on such ligand-exhibiting cells.

Depending on the specific conditions being treated, agents may be formulated and administered systemically or locally. Techniques for formulation and administration may be found in "Remington's Pharmaceutical Sciences," Mack Publishing Co., Easton, Pa., latest edition. Suitable routes may include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

RPTPases and/or their ligands may also be used to screen for additional molecules that can act to modulate the activity of cellular processes such as those described above. For example, compounds that bind to RPTPase molecules may be identified. Such compounds may include, but are not limited to anti-RPTPase antibodies. One method that may be pursued in the isolation of such RPTPase-binding molecules would include the attachment of RPTPase molecules to a solid matrix, such as agarose or plastic beads, microtiter wells, or petri dishes, and the subsequent incubation of attached RPTPase molecules in the presence of a potential RPTPase-binding compound or compounds. After incubation, unbound compounds are washed away, and the RPTP-bound compounds are recovered. In this procedure, large numbers of types of molecules may be simultaneously screened for RPTPase-binding activity. Bound molecules could be eluted from the RPTPase molecules by, for example, competing them away from the RPTPase molecules with the addition of excess ligand.

The effect of a compound on the phosphatase activity of RPTPase molecules can also be determined. Such a compound may, for example, be one isolated using a procedure such as the binding technique described above. One method that may be utilized for determining the effects of a compound on RPTPase phosphatase activity would involve exposing such a compound to a preparation of cultured cells that express the RPTPase of the invention, and subsequently measuring the phosphatase activity of the culture. The compound of interest may be introduced to the cells, for example, by addition of the compound to the tissue culture medium. The phosphatase activity of the cells within the tissue culture preparation may be determined by measuring the level of cellular phosphotyrosine within the culture, using method that are well known in the art (Honegger et al., 1987, Cell 51:199–209; Margolis et al., 1989, Cell 57:1101–1107). To properly determine the effects of addition of the compound, the cellular phosphotyrosine levels of the same type of tissue culture preparation that has not been exposed to this compound must also be measured, and the two levels must then be compared. For example, RPTPases may be incorporated into apparatuses including but not limited to affinity columns such that large numbers of molecules may be screened quickly by being applied to said apparatuses. Those molecules with an affinity for RPTPases will be bound. Such binding will also bring about a partial purification of the molecules of interest. In order to continue the purification process, the bound molecules should be eluted off the above described apparatuses, for example by competing them away from the RPTPases with excess ligand, and the process should be repeated until the molecule of interest is purified to the extent necessary.

6. EXAMPLE

Characterization of the Receptor Protein Tyrosine Phosphosphatase RPTPβ

The subsections below describe the characterization of a human receptor protein tyrosine phosphatase molecule, RPTPβ. It is shown that this RPTPβ contains an extracellular carbonic anhydrase domain and is a proteoglycan. In addition, it is shown that RPTPβ mRNA and protein are predominantly expressed in brain tissue.

6.1 Materials and Methods

6.1.1 Isolation of cDNA Clones and DNA Sequence Analysis

A cDNA clone containing a portion of the coding sequences for RPTPβ was isolated after screening a λgt11 human infant brain stem cDNA library under conditions of reduced stringency with a nick translated LCA probe that included both phosphatase domains (Kaplan, R. et al., 1990, Proc. Natl. Acad. Sci. USA 87:7000–7004). Since the 5' end of this gene was not present in the original clone, the library was rescreened with a DNA fragment that was generated from the 5' end of the original clone. The probe was labeled with $^{32}$P dCTP utilizing the random prime method (USB) and hybridization was performed under moderately stringent conditions at 42° C. in a buffer containing 50% formamide, 5×SSC, 20 mM Tris-CL pH 7.6, 1X Denhardt's solution, 0.1% SDS and 100 μg/ml of sheared and denatured salmon sperm DNA. After hybridization, phage filters were washed three times for 20 min at 50° C. in a buffer containing 0.1×SSC/0.1% SDS and then were processed for autoradiography. The brainstem library was rescreened a total of three times in order to isolate overlapping cDNA clones that contained the entire coding sequence for RPTPβ.

cDNA inserts from positive recombinant plaque-purified were subcloned into the plasmid vector, Blue Script (Stratagene), and sequenced by the dideoxy chain termination method using the Sequenase Version 2.0 Kit (USB).

6.1.2 Chromosmal Localization

Figure 2B:
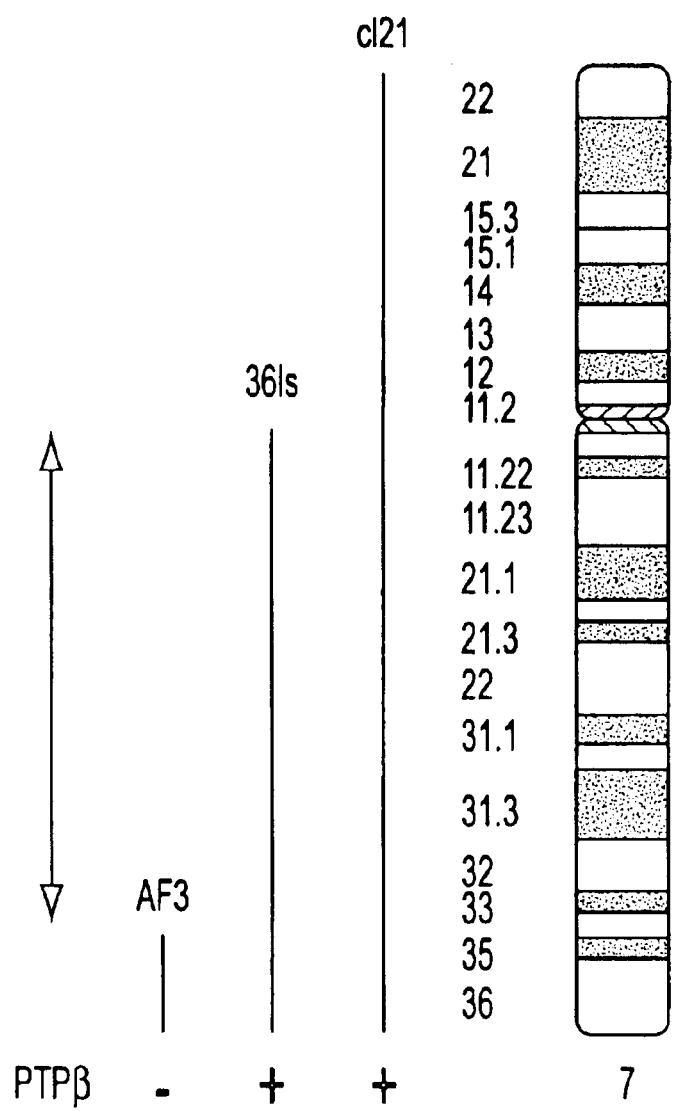

Isolation, propagation and characterization of parental and somatic cell hybrids used in this study have been described (Durst, M. et al., 1987, Proc. Natl. Acad. Sci USA 84:1070–1074). Presence of specific human chromosomes or regions of chromosomes has been confirmed by DNA hybridization using probes for genes assigned to specific chromosome regions. FIG. 2A depicts diagrammatically the chromosomes or partial chromosomes retained in most of the hybrids used.

Chromosomal in situ hybridization was performed as described previously (Cannizzano, L. A. et al., 1991, Cancer Res. 51:3818–3820). Slides containing metaphase chromosomes from normal male (46 XY) peripheral blood lymphocytes were aged at 4° C. for 7–10 days and pretreated with ribonuclease A (Sigma) for 1 hour at 37° C. The chromosomal DNA was denatured in a hybridization mixture containing 50% formamide, 2×SSC and 10% dextran sulfate (pH 7.0). Hybridization was carried out at 37° C. overnight. After rinsing at 39° C. in three changes of 50% formamide and 2×SSC, then five changes of 2×SSC, slides were dehydrated, air dried, subjected to autoradiography, and banded with Wright's -Giemsa stain solution mixed with 1–3 parts of pH 9.2 borate buffer (Cannizzano, L. A. et al., 1991, Cancer Res. 51:3818–3820).

6.1.3 Isolation of Mouse Sequences Homologous to Human RPTPβ

Two oligonucleotides in conserved phosphatase domain II were synthesized according to the nucleotide sequence of human RPTPβ. These oligos, in conjunction with phage DNA from a mouse brain cDNA library that was purchased from Clonetech (Palo Alto, Calif.), were used in the polymerase chain reaction with Taq polymerase (Perkin-Elmer) to amplify homologous mouse RPTPβ sequences. The amplified product was purified and cloned into the Blue Script plasmid vector (Stratagene, La Jolla, Calif.). Homology was confirmed by DNA sequence analysis as described above. This subcloned fragment will be referred to as pBSMBDII.

6.1.4 Northern Analysis

Total cellular RNA was prepared with the Strategene RNA isolation kit. Poly A$^+$RNA was further selected utilizing oligo dT cellulose chromatography (Stratagene). For Northern analysis, the RNA was separated on a 1.0% agarose/2.2 M formaldehyde gel and transferred to a Nytran membrane (Schleicher and Schuell) by capillary action. The membrane was prehybridized and hybridized in 0.5 M sodium phosphate pH 7.2, 7% SDS, 1 mM EDTA, 100 µg/ml salmon sperm DNA and then washed in 40 mM sodium phosphate ph 7.2, 1% SDS, 1 mM EDTA at 65° C. For the blot containing RNA isolated from various mouse tissues, a $^{32}$P-labeled probe was made utilizing pBSMBDII as template in the random prime labeling reaction (USB). The human glioblastoma and neuroblastoma RNA blots were probed with labeled restriction fragments isolated from different parts of the human RPTPβ cDNA clones.

6.1.5 Antibodies

A peptide derived from the carboxy-terminal 15 amino acids of human RPTPβ was synthesized and coupled to Keyhole limpet hemocyanin according to previously published procedures (Harlow, E. and Lane, D., 1988, in Antibodies: A Laboratory Manual, Cold Spring Harbor Laboratory Press, Cold Spring Harbor, N.Y., pp. 77–88). This was used as immunogen to inoculate two rabbits to produce polyclonal antisera against RPTPβ. Anti-EGF receptor immunoprecipitates were performed with RK2 antibody which recognizes the glycosylated and nonglycosylated forms of the EGF receptor (Kris, R. M. et al., 1985, Cell 40: 619–625).

6.1.6 Cell Labeling and Immunoprecipitation

The human neuroblastoma cell line, Lan 5, was maintained in Dulbecco's modified Eagles medium (DMEM) contain 10% fetal bovine serum (FBS). Cell treatment with tunicamycin involved incubating the cultures with 10 µg/ml tunicamycin (Sigma) for 1 hour prior to $^{35}$S methionine labeling. Treated and untreated cells were washed twice with methionine free DMEM and then labeled for 4 hours with 0.15 mCi/ml $^{32}$S methionine (purchased from New England Nuclear) in DMEM minus methionine containing 1% dialyzed FBS. During the labeling period, 10 µG/ml tunicamycin was added to the medium of the treated cells. Cells were then washed with ice cold phosphate-buffered saline and solubilized in a lysis buffer containing Hepes (N'-2-hydroxyethylpiperazine-N'-2-ethane-sulfonic acid) pH 7.5, 150 mM NaCl, 1.0% Triton X-100, 10% glycerol, 1.5 mM MgCl$_2$ 1 mM ethylene glycol-bis (B-aminoethyl ether)-N, N, N', N'-tetracetic acid (EGTA), 10 µg leupeptin per ml, 1 mM phenylmethylsulfunyl fluoride, and 10 µg aprotinin per ml. For $^{35}$S-NaSO$_4$ labeling, cells were washed twice with phosphate-buffered saline (PBS), at which time labeling mix was added (NEX-041H medium plus 10% calf serum, gentamicin, and 200 µCi/ml of $^{35}$S-NaSO$_4$). Cells were labeled for 20 hours, washed twice with PBS, and solubilized as described above. Cell lysates were clarified and then immunoprecipitated. Lysates from $^{35}$S-Methionine-labeled cultures were immunoprecipitated with normal rabbit antiserum, anti-RPTPβ antiserum or RK2 antiserum for 2 hours at 40° C. Lysates from $^{35}$S-NaSO$_4$-labeled cultures were immunoprecipitated without preclearing, with anti-RPTPβ antiserum for 2 hours at 4° C. The immunocomplexes were then precipitated with Protein A Sepharose (Sigma) for 45 min at 4° C. and washed 10 times with RIPA buffer (20 mM Tris-Cl ph 7.6, 300 mM NaCl, 2 mM EDTA, 1.0% Triton X-100, 1.0% sodium deoxycholate and 0.1% SDS). The immunoprecipitated material was analyzed on SDS-polyacrylamide gels (7.5% for $^{35}$S-Methionine, 5% for $^{35}$S-NaSO$_4$) and then fluorographed.

6.1.7 In Situ Hybridization Analysis

Fresh frozen tissue was cut on a cryostat into 20 µm thick sections and thaw mounted onto gelatin coated slides. The sections were fixed in 4% paraformaldehyde in 0.1 M sodium phosphate (pH 7.4) for 30 min and rinsed 3× for 5 min each in 0.1 M sodium phosphate and 1× for 10 min in 2×SSC. The probe used in the hybridization analysis was a 49 base oligonucleotide complementary to a portion of the RPTPβ mRNA in phosphatase Domain II. The oligonucleotide was labeled with [α-$^{35}$S] dATP (NEN Dupont) using terminal deoxynucleotidyltransferase (Boerhinger Mannheim) and purified using Sephadex G25 quick spin columns (Boerhinger Mannheim). The specific activity of the labeled probes was between $5 \times 10^8$–$1 \times 10^9$ cpm/µg. Prehybridizations and hybridizations were carried out in a buffer containing 50% deionized formamide, 4×SSC, 1×Denhardt's, 500 µg/ml denatured salmon sperm DNA, 250 µg/ml yeast tRNA and 10% dextran sulfate. The tissue was incubated for 12 h at 45° C. in hybridization solution containing the labeled probe ($1 \times 10^6$ cpm/section) and 10 mM dithiothreitol (DTT). Controls for specificity were performed on adjacent sections by diluting the labeled oligonucleotides with a 30 fold concentration of the appropriate unlabeled oligonucleotide and by hybridization with a sense probe. After hybridization the sections were washed in 2 changes of 2×SSC at room temperature for 1 h, 1×SSC at 55° C. for 30 min., 0.5×SSC at 55° C. for 30 min, 0.5×SSC at room temperature for 15 min and dehydrated in 60%, 80%, and 100% ethanol. After air drying, the sections were exposed to X-ray film for 5–10d.

6.2 Results

6.2.1 The Primary Amino Acid Sequence of RPTPβ

Four overlapping cDNA clones were isolated from the human brain stem library that contained the entire coding sequence for RPTPβ. The primary amino acid sequence deduced from the nucleotide sequence of the cDNA clones is shown in FIG. 1. RPTPβ belongs to the high molecular weight, transmembrane class of tyrosine phosphatases and is encoded by 2308 amino acids. The protein contains a signal peptide (underlined in FIG. 1) followed by a long extracellular domain of 1636 amino acids containing 21 potential N-glycosylation sites (indicated by the arrows). A hydrophobic, transmembrane peptide (bold sequences) joins the extracellular portion of the protein to two tandemly repeated and conserved phosphatase domains (designated DI and DII).

6.2.2 Chromosomal Localization of Human RPTPβ

The chromosomal localization of the human RPTPβ gene was initially determined utilizing a panel of rodent-human hybrids carrying defined human chromosomes or chromosome regions. DNAs from seventeen rodent-human hybrids, carrying overlapping subsets of human chromosome regions representing the entire human genome (see FIG. 2A) were cleaved with Eco RI, electrophoresed, transferred to filters and hybridized to the radiolabelled human RPTPβ probe. Results are summarized in FIG. 2A in which it can be seen that the presence of human chromosome 7. A more precise localization of the RPTPβ gene was determined by chromosomal in situ hybridization to metaphase chromosomes of normal human lymphocytes. This technique places the RPTPβ gene at 7q31-33 with the most likely position at 7q31.3–7q32, which is diagrammatically shown to the right of the chromosome 7 sketch in FIG. 2B.

6.2.3 Northern Blot Analysis

Northern hybridization analysis of various murine tissue RNAs was performed to determine the tissue specific expression of RPTPβ. The probe used in this analysis was a portion of the murine homolog of RPTPβ that was amplified in the polymerase chain reaction (see Materials and Methods) and contains 405 nucleotides encoding 135 amino acids of Domain II. Based on a nucleotide sequence comparison to the equivalent region of the human cDNA clone, the murine and human clones are 88% identical at the nucleotide level in this region of Domain II of RPTPβ. The results of this Northern analysis (FIG. 3A) indicate the presence of two major transcripts of 8.8 and 6.4 kb, respectively. A minor transcript of greater than 9.4 kb is sometimes observed and might represent cross-reaction to a highly related phosphatase. Both the transcripts are restricted to brain tissue, and could not be detected in other tissue. The absence of expression of RPTPβ in the majority of tissues is not due to degraded RNA since the presence of intact actin transcripts was observed utilizing the same blot (FIG. 3B).

Because the expression of RPTPβ was restricted to brain tissue, expression of this phosphatase in different human glioblastoma cell lines and a human neuroblastoma cell line, Lan 5, was examined. A human RPTPβ probe hybridized to three major transcripts of 8.8, 7.5 and 6.4 kb respectively (FIG. 3C). These transcripts were only detected in RNA isolated from the Lan 5 neuroblastoma cell line and were absent in the RNA isolated from the four glioblastoma cell lines even though similar amounts of total cellular RNA were loaded as determined from ethidium bromide staining of the 28S and 18S ribosomal RNAs. The 8.8 and 6.4 kb transcripts were identical in size to the two transcripts observed in RNA isolated from mouse brain tissue (FIG. 3A). The presence of three transcripts in Lan 5 RNA could be due to cross hybridization with other highly related phosphatases since the probe used in this analysis was derived from sequences in the conserved phosphatase Domain I or be due to alteratively spliced RPTPβ transcripts. In order to obtain further insight into the nature of the three RPTPβ transcripts, a similar Northern analysis was performed on RNA isolated from Lan 5 cells with probes isolated from the 5' portion of the human cDNA clones. The probes utilized were derived from sequences in the extracellular domain that are unique for RPTPβ. This analysis showed an identical pattern of hybridization as what is observed in FIG. 3C. These results suggest that the three distinct transcripts are products of alternatively spliced mRNAs.

6.2.4 Identification of a Variant Form of RPTPβ

Figure 4A:
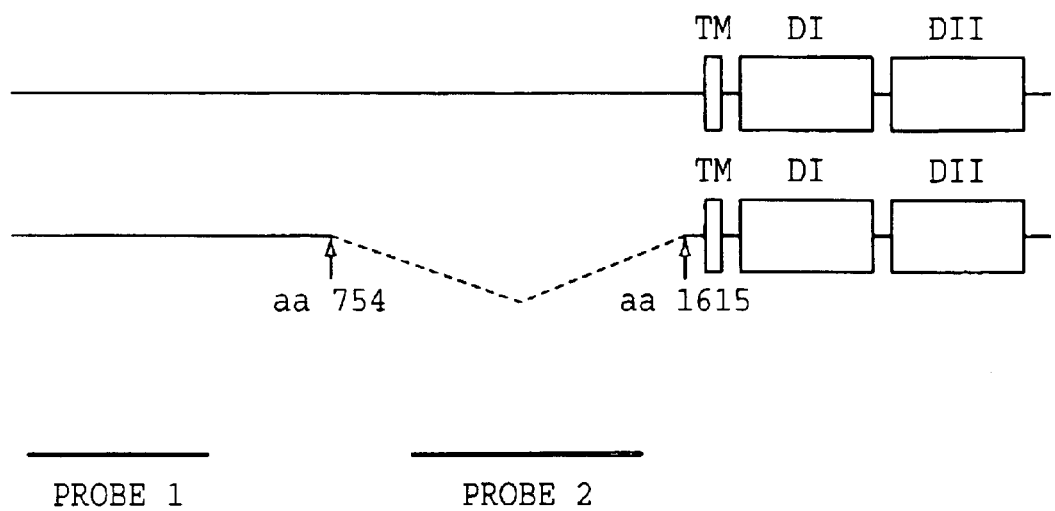
Figure 4B:
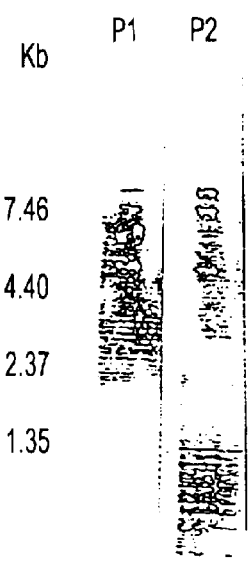

The overlapping human cDNA clones collectively contain greater than 8.1 kb of coding and noncoding sequences and appear to represent the largest transcript that is 8.8 kb in length. In screening the human brain stem library and another human caudate library (Stratagene), two independent cDNA clones, called BsdlI and CaudlI, were isolated that each contained an identical deletion of 2581 nucleotides from the extracellular domain of RPTPβ. This deletion did not introduce a stop codon or interrupt the open reading frame of RPTPβ and joined amino acid 754 to amino acid 1615 as shown in FIG. 4A. The deleted clones maintained the same extreme 5' and 3' ends of the RPTPβ gene in addition to the sequences encoding the transmembrane peptide and the two phosphatase domains. A transcript corresponding to the deleted clone would be approximately 2.6 kb smaller than the transcript corresponding to the undeleted, full-length clone. As shown in FIG. 3C, there is a transcript of 6.4 kb that is approximately 2.4 kb smaller than the largest transcript which is 8.8 kb in length. In order to determine whether the 6.4 kb transcript represents the deleted form, Northern blot hybridization analysis was performed utilizing RNA isolated from the Lan 5 cell line. Duplicate blots were made from this RNA and hybridized with two distinct probes. One probe (probe 1) was derived from sequences in the 5' end of RPTPβ that are present in the deleted and full length cDNA clones. The other probe (probe 2) encompasses the sequences that are no longer present in the deleted cDNA clones. The location of probes A and B in the full length RPTPβ cDNA is shown in FIG. 4A. Comparison of the Northern analysis with the two probes revealed that probe 1 hybridized to the three distinct transcript (FIG. 4B, P1) whereas probe 2 hybridized to the 7.5 and 8.8 kb transcripts but failed to hybridize to the 6.4 kb transcript (FIG. 4B, P2). These results provide preliminary evidence that the 6.4 kb transcript represents a deleted and alternatively spliced form of RPTPβ. The nature of the 7.5 kb transcript remains to be determined.

6.2.5 In Situ Hybridization Analysis

Figure 5B:

In order to obtain further insight into the expression of RPTPβ, an in situ hybridization analysis was performed to look for the expression of RPTPβ in the developing mouse embryo. Studies were also performed to determine whether RPTPβ gene expression is diffuse or restricted to specific regions of the adult brain. The results of this analysis confirm that RPTPβ is preferentially expressed in the central nervous system. In the day 20 mouse embryo (E20), high level of expression was observed in the ventricular zone of the brain (FIG 5A.) and in the spinal cord. A similar pattern of expression, with variable levels of intensity, has been seen from embryonic day 13 to postnatal day 7. The level of expression is much lower in the adult brain, and is discretely localized to the Purkinje cell layer of the cerebellum, the dentate gyrus, and the anterior horn of lateral ventricle (FIG. 5B). The addition of a 30 fold excess of unlabeled oligonucleotide completely blocked the labeling in all of these areas indicating that this probe is hybridizing to mRNA in a sequence specific manner. Results from the Northern blot and in situ hybridization analyses demonstrate that RPTPβ has a restricted tissue specificity to specific regions in the central nervous system and therefore may play an important role in the development of the nervous system.

6.2.6 Endogenous RPTPβ Protein Expression

Since RPTPβ transcripts were identified in the Lan 5 neuroblastoma cell line, these cells were subsequently used to detect endogenous protein expression. Cell lysates prepared from cultures labeled with $^{35}$S-methionine for 4 hours were immunoprecipitated with normal rabbit serum or anti-RPTPβ antiserum (FIG. 6). A protein with apparent weight of approximately 300 kd was recognized by the immune but not by the normal rabbit serum (lanes 1 and 2). Since there are 21 potential N-glycosylation sites, it was necessary to determine whether the protein immunoprecipitated by the anti-RPTPβ antiserum represented the core protein or a glycosylated form of the protein. In order to do this, tunicamycin was added to the cells during the $^{35}$S-methionine labeling period. The effects of tunicamycin treatment on RPTPβ mobility was compared to the cell line were drug's ability to inhibit the glycosylation of the EGF receptor, which is also expressed in this cell line. Untreated cell lysates and lysates prepared from cells treated with tunicamycin were immunoprecipitated with an antibody (RK2) that recognizes the 170 kd glycosylated form and the 135 kd nonglycosylated form of the EGF receptor. (Kris, R. M. et al., 1985, Cell 40:619–625; and FIG. 6, lanes 4 and 5). The protein immunoprecipitated with anti RPTPβ antiserum from Lan 5 cells, that had been metabolically labeled in the presence of tunicamycin, migrated-faster than the immunoprecipitated product isolated from the untreated cells (compare lanes 3 and 2). The molecular weight of the protein detected in FIG. 6, lane 3, is approximately 250 kD a value consistent with that of the core protein whose predicted molecular weight as deduced from the amino acid sequence is approximately 254 kd.

6.2.7 The Presence of Carbonic Anhydrase Related Sequences In The Extracellular Domain of RPTPβ

A stretch of 283 amino acids in the extracellular domain of a related transmembrane-type phosphatase, RPTPγ that shares homology with different isoforms of the enzyme carbonic anhydrase (CAH) has recently been identified. A similar stretch of CAH-related amino acids in RPTPβ has now been identified at the extreme amino terminus of the protein (designated as CAH-like in FIG. 1). Alignment of the CAH-related domains of RPTPβ and RPTPγ with the six known isoforms of CAH is shown in FIG. 7A. FIG. 7B shows the percent similarity, taking into account conservative amino acid substitutions between the CAH-related domain of RPTPβ and the corresponding domain of RPTPγ and the six CAH enzymes. The CAH-related domain of RPTPβ ranges anywhere from 45–50% in amino acid sequence similarity to the six different isoforms of CAH. The highest degree of similarity (58%) exists between the CAH-related sequences of RPTPβ and RPTPγ. Therefore it appears that RPTPases, β and γ, may represent a new subgroup of tyrosine phosphatases that will be characterized by the presence of CAH-related sequences in their extracellular domains.

6.2.8 RPTPβ is a Proteoglycan

In this series of experiments, it is demonstrated that RPTPβ exhibits the characteristics of a proteoglycan. Specifically, it is shown that the RPTPβ protein is covalently modified with high molecular weight, sulfate-containing moieties, and that such moieties are sensitive to chondroitinase ABC treatment.

6.2.8.1 $^{35}$Sulfate Labeling

In order to begin to address what post-translational modifications RPTP: undergoes, 293 cells transfected with RPTPβ DNA as well as control, 293 cells transfected with vector alone were $^{35}$S-NaSO$_4$ labeled. Immunoprecipitations of the lysates, using an anti-RPTPβ antiserum were then performed. The gel illustrated in FIG. 8 shows the results of one such immunoprecipitation. As can be seen in lane 3, a significant amount of labeled material that reacts with the RPTPβ antiserum does not enter the running portion of the gel. This is easily contrasted to the non-transfected control lysate in lane 4, in which no such material is detectable.

6.2.8.2 $^{35}$S-Methionine Labeling

In continuing to investigate the posttranslational modifications that RPTPβ undergoes, 293 cells transfected with RPTP3 DNA as well as control 293 cells transfected with vector alone were $^{35}$S-methionine labeled. Immunoprecipitations of the lysates, using an anti-RPTPβ antiserum were then performed. The gel illustrated in FIG. 9 shows the results of one such immunoprecipitation. Lane 4 contains a large amount of labeled material that reacted with the anti-RPTPβ antiserum which does not enter the running portion of the gel and a significant amount that does not even enter the stacking portion of the gel. By contrast, lane 5, which contains the control lysate, exhibits no such material.

6.2.8.3 Chondroitinase Treatment 293 cells transfected with RPTPβ DNA as well as control 293 cells transfected with vector alone were $^{35}$S-methionine labeled. Lysates were immunoprecipitated using an anti-RPTPβ antiserum and then chondroitinase ABC treated for 1 hour. The gel illustrated in FIG. 10 shows the results of one such immunoprecipitation. Lane 3 and 4 contain non-treated and treated RPTPβ-transfected lysates, respectively. As can be seen, the bulk of the labeled material that had not entered the gel in the non-treated sample is absent in the treated sample, and in its place, a labeled band of a lower molecular weight has appeared. In lanes 1 and 2 are non-treated and treated control lysates, respectively. No such shift in high molecular weight labeled material is detectable here.

7. EXAMPLE

The Cell Adhesion Molecules, N-CAM and Ng-CAM Are Ligands of the Receptor Protein Tyrosine Phosphatase RPTPβ

The experiments described below demonstrate that a receptor protein tyrosine phosphatase, the human RPTPβ molecule, binds the cell adhesion molecules N-CAM and Ng-CAM. Section 7.2.1 demonstrate that the rat proteoglycan, 3F8, binds these two CAM molecules. Section 7.2.2, demonstrates that the carbonic anhydrase domains of rat 3F8 and human RPTPβ are nearly identical, leading to the conclusion that RPTPβ is the human counterpart of the rat proteoglycan 3F8. When taken together, these two pieces of information, indicate that RPTPβ also binds the two CAM molecules, N-CAM and Ng-CAM.

7.1 Materials and Methods

7.1.1 Proteins and Antibodies

Ng-CAM and N-CAM were purified from 14-d embryonic chicken brains by immunoaffinity chromatography using specific monoclonal antibodies (Grumet, M. and Edelman, G. M., 1988, J. Cell Biol. 106:487–503). Analysis of the proteins on SDS/PAGE showed that Ng-CAM consisted of a major component of 135 kDa and lesser amounts of the 200 kDa and 80 kDa species as described (Grumet, M. and Edelman, G. M., 1988, J. Cell Biol. 106:487–503) and N-CAM ran as heterodisperse species above 12 kDa as described previously (Hoffman, S. et al., 1982, J. Biol. Chem. 257:7720–7729).

Chondroitin sulfate proteoglycans were extracted with PBS from the brains of 7-day or 2- to 2-month old Sprague-Dawley rats, and purified by ion exchange chromatography and gel filtration (Kiang, W.-L. et al., 1981, J. Biol. Chem. 256:10529–10537). 3F8 proteoglycan was then isolated by immunoaffinity chromatography, using monoclonal antibodies coupled to CNBr-activated Sepharose 4B (Rauch, U. et al., 1991, J. Biol. Chem. 266:14785–14801). Analysis of the proteins on SDS-PAGE following chondroitinase-treatment showed that the core glycoprotein obtained by chondroitinase treatment of the 3F8 proteoglycan from either early postnatal or adult brain migrated on SDS-PAGE as a single bad at 400 kDa (Rauch, U. et al., 1991, J. Biol. Chem. 266:14785–14801).

For studies of the core proteins, proteoglycans were digested for 45–60 min at 37° C. with protease-free chondroitinase ABC (Seikagaku America Inc., Rockville, MD) in 100 mM Tris-HCl buffer (pH 8.0 at 37° C.) containing 30 mM sodium acetate. A ratio of 1.5 mM chondroitinase/$\mu$g proteoglycan protein was used for the 3F8 proteoglycan. Completeness of digestion was confirmed by SDS-PAGE, which demonstrated that the large native proteoglycan which did not enter the separating gel was converted to discrete core glycoprotein bands after enzyme treatment (Rauch, U. et al., 1991, J. Biol. Chem. 266:14785–14801).

Polyclonal rabbit antibodies raised against chicken Ng-CAM were prepared as previously described (Grumet, M. et al., 1984, Proc. Natl. Acad. Sci USA 81:267–271).

7.1.2 Covasphere Aggregation

Proteins (50 $\mu$g) were covalently coupled to 200 $\mu$l of 0.5-$\mu$m Covaspheres (Duke Scientific Corp., Palo Alto, Calif.), washed twice in PBS containing 1 mg/ml BSA/10 mM NaN$_3$, and resuspended in 200 $\mu$l of buffer as previously described (Grumet, M. and Edelman, G. M., 1988, J. Cell Biol. 106:487–503). Quantitative measurements indicated that under these conditions approximately 20% of the Ng-CAM protein was bound to the Covaspheres. For Covasphere aggregation experiments, prior aggregates in the bead preparations were first dissociated by sonication for 10–20 sec, and 6 $\mu$l aliquots (containing about 0.3 $\mu$g of protein) were mixed with 54 $\mu$g of PBS containing the indicated amounts of proteins. After a 30 min incubation on ice, the samples were resonicated and aggregation was monitored at 25° C. The appearance of superthreshold aggregates of Covaspheres was measured using a Coulter Counter (Model ZBI) fitted with a 100 $\mu$m aperture set at amplication=0.17, aperture current=0.33, threshold 10–100; these settings allowed detection of particles>–4 $\mu$m as described previously (Grumet, M. and Edelman, G. M., 1988, J. Cell Biol. 106:487–503). Superthreshold particles were measured in samples of 20 $\mu$l that were diluted into 20 ml of PBS. To test the sensitivity of proteoglycans to proteolysis, solutions containing 0.1 mg/ml proteoglycan were treated with 10 $\mu$g/ml of trypsin for 1 h at 37° C. and the reaction was terminated by addition of 20 $\mu$g/ml of soybean trypsin inhibitor.

7.1.3 DNA Sequencing

Sequencing was performed according to standard dideoxy techniques.

7.2 Results

7.2.1 The Rat Proteoglycan, 3F8, Binds CAMS

In previous studies, it was found that Ng-CAM (Grumet, M. and Edelman, G. M., 1988, J. Cell Biol. 106:487–503) and N-CAM (Hoffman, S. and Edelman, G. M., 1983, Proc. Natl. Acad. Sci. USA 80:5762–5766) individually mediated homophilic binding when reconstituted into liposomes or when covalently bound to the surface of beads (Covaspheres). The rate of aggregation of Ng-CAM-Covaspheres was measured using a Coulter Counter to detect aggregates larger than a given size and was shown to be highly dependent on the concentration of Covaspheres in suspension; It was previously determined that at a concentration of ~85 cm$^2$ of bead surface area/ml, the appearance of aggregates began to reach a plateau level after ~1 h of incubation (Grumet, M. and Edelman, G. M., 1988, J. Cell Biol. 106:487–503). Therefore, to explore potential interaction between proteoglycans and CAMs, the effects of various proteins and proteoglycans on the rate of aggregation of Ng-CAM-Covaspheres were tested. Whereas control proteins including BSA and fibronectin did not inhibit aggregation of the Ng-CAM-coated beads, one distinct chondroitin sulfate proteoglycan, 3F8, inhibited aggregation (FIG. 11). In contrast, aggrecan, a rat chondrosarcoma chondroitin sulfate proteoglycan (Doege, K. M. et al, 1987, J. Biol. Chem. 262:17757–17767) did not inhibit the aggregation, indicating that the effects were not simply related to the presence of chondroitin sulfate. This conclusion was further supported by the finding that the core glycoproteins obtained by chondroitinase treatment of the proteoglycans were equally effective in inhibiting the aggregation of Ng-CAM-Covaspheres (FIG. 12). In contrast, most of the inhibitory activity was eliminated after treating the proteoglycans with trypsin (see Materials and Methods, Section 7.1.2). These results demonstrate that the effects of the 3F8 proteoglycan on Ng-CAM binding are not mediated by the glycosaminoglycan chains, but that a protein domain (or possibly a cluster of oligosaccharides present on the proteoglycan core protein) is involved. Based on these results, all further experiments were performed using chondroitinase-treated proteoglycans.

The 3F8 proteoglycan inhibited aggregation of Ng-CAM-Covaspheres at 30 $\mu$g/ml (FIG. 11). It is unlikely that the proteoglycans inhibited Covasphere aggregation by a trivial mechanism such as proteolysis of Ng-CAM because it was found that incubation of the 3F8 proteoglycan with Ng-CAM for 1 h at 37° C. had no effect of the molecular sizes of the Ng-CAM components when resolved by SDS-PAGE.

To compare the effects of different proteoglycans we measured the appearance of superthreshold aggregates of Covaspheres using a Coulter Counter to detect aggregates larger than a given size. The aggregation of Ng-CAM-Covaspheres was inhibited in a concentration-dependent manner by the 3F8 proteoglycan (FIG. 12).

To determine whether the proteoglycans could affect other CAMs, a similar series of experiments was performed using N-CAM coated beads. The aggregation of N-CAM-Covaspheres was inhibited in a concentration-dependent manner in the presence of the 3F8 proteoglycan (FIG. 13). These results are similar to those obtained using Ng-CAM-Covaspheres, (compare to FIGS. 11 and 12).

The inhibitory effect of 3F8 proteoglycan on the aggregation of Ng-CAM- and N-CAM-coated beads were maximal at approximately 10 $\mu$g/ml. In a typical assay (60 $\mu$l) at this concentration of proteoglycans, the amount of proteoglycan in solution was 0.6 $\mu$g and the amount of Ng-CAM on the Covaspheres was approximately 0.3 $\mu$g (see Materials and Methods, Section 7.1.2), suggesting that the brain proteoglycan can perturb homophilic Ng-CAM binding at approximately stoichiometric levels with Ng-CAM.

7.2.2 RPTP$\beta$ Represents the Human Counterpart of the Rat Proteoglycan, 3F8

Comparison of the sequence of human RPTP$\beta$ with a partial sequence of a proteoglycan designated 3F8 cloned from a rat brain stem library (R. Margolis, personal communication), reveals that these two proteins contain carbonic anhydrase-like domains and are 91.9% identical at the amino acid level (FIG. 14). The maximum amino acid sequence identity between the different members of the carbonic anhydrase family of enzymes is 64%. This sequence information indicates that the two proteins, the murine proteoglycan 3F8 and the human proteoglycan RPTPβ, are counterparts of each other.

8. EXAMPLE

The Extracellular Matrix Molecule Tenascin is a Ligand of The Receptor protein Tyrosine phosphatase RPTPβ

The experiments described below demonstrate that a receptor protein tyrosine phosphatase, the human RPTPβ molecule, binds the extracellular matrix molecule tenascin. Section 8.2 demonstrates that the rat proteoglycan, 3F8, binds tenascin. Section 7.2.2, above, demonstrates that the carbonic anhydrase-like domains of rat 3F8 and of human RPTPβ are nearly identical, leading to the conclusion that RPTPβ is the human counterpart of the rat proteoglycan 3F8. When taken together, these two pieces of information indicate that RPTPβ also binds tenascin molecules.

8.1 Materials And Methods

8.1.1 Protein And Antibodies

Tenascin (Telios) purity was determined by SDS-PAGE gel analysis.

3F8 chondroitin sulfate proteoglycan. Rat brain 3F8 chondroitin sulfate proteoglycan was prepared according to Rauch et al. (Rauch, U. et al., 1991, J. Biol. Chem. 266:14785–14801).

Ng-CAM . Chicken brain Ng-CAM was purified as described in Grumet and Edelman (Grumet, M. and Edelman, G. M., 1988, J. Cell Biology 106:487–503). Briefly, Ng-CAM was purified from detergent extracts of 14 day embryo brains by immunoaffinity chromatography using monoclonal antibodies (3G2; Rieger, F. J. et al., 1986, J. Cell Biol. 103:379–391) against Ng-CAM. 1 mM PMSF (phenylmethylsulfonyl fluoride) was added to retard proteolysis.

Aggrecan. Aggrecan, a chondroitin sulfate proteoglycan derived from cartilage, was prepared according to Grumet et al. (Grumet, M. et al., 1993, J. Cell Biol. 120:815–824). Briefly, the chondroitin sulfate PG was extracted from a transplantable rat chondrosarcoma (Choi, H. U. et al., 1971, Proc. Natl. Acad. Sci. USA 68:877–879) and isolated by CsCl density gradient centrifugation (Faltz, L. L. et al., 1979, J. Biol. Chem. 254:1375–1380).

3F8 monoclonal antibody. Prepared according to Rauch et al., 1991, J. Biol. Chem. 266:14785–14801.

8.1.2 Covasphere Preparation And Aggregation

Covaspheres were prepared as described in Grumet et al., 1993, J. Cell Biol. 120:815–824. Briefly, proteins (50 µg) were covalently coupled to 200 µl 0.5 µm Covaspheres (Duke Scientific Corp., Palo Alto, Calif.), washed twice in PBS containing 1 mg/ml BSA, and 10 mM NaN$_3$, and resuspended in the original buffer volume. Covaspheres as supplied by the manufacturer were at a concentration of 850-cm$^2$ surface area/ml.

For Covasphere aggregation experiments, pre-existing aggregates in the bead preparations were first dissociated by sonication for 10–20 seconds. After a 30 minute incubation on ice, samples were resonicated and aggregation was monitored at 250° C.

Fluorescent-Covaspheres were visualized using a Nikon Diaphot with a filter capable of discriminating between fluorescein and rhodamine.

8.2 Results

In the experiments presented in this Section, representative results of which are presented in FIG. 15, it is shown that the proteoglycan 3F8 binds the extracellular matrix molecule tenascin. For these experiments, red-fluorescing tenascin-coated Covaspheres were prepared as described in Section 8.1.1, above, and mixed with various green-fluorescing Covaspheres. Such green-fluorescing Covaspheres were coated with either 3F8 chondroitin sulfate brain proteoglycan (PG), aggrecan (a chondroitin sulfate PG derived from cartilage), or Ng-CAM (a neural cell adhesion molecule). All green-fluorescing Covaspheres were prepared according to the methods described, above, in Section 8.1.1.

First, tenascin-coated Covaspheres were mixed with 3F8 PG-coated Covaspheres, either in the absence (Panel 1) or presence (Panel 2) of a 3F8 monoclonal antibody. As can be seen in FIG. 15, Panel 1, tenascin-coated Covaspheres (left, red-fluorescing) and 3F8 PG-coated Covaspheres (right, green-fluorescing) aggregates are nearly identical, indicating that tenascin binds 3F8 PG. FIG. 15, Panel 2 illustrates that the tenascin-coated Covasphere/3F8 PG-coated Covasphere binding and coaggregation is disrupted in the presence of 3F8 PG monoclonal antibody. The use of a nonimmune antibody had no effect on tenascin/3F8 Covasphere coaggregation, indicating the specificity of tenascin/3F8 PG interaction.

Tenascin-coated Covaspheres were also mixed with aggrecan-coated Covaspheres the results of which are shown in FIG. 15, Panel 3. As can be seen, little or no self-aggregation was observed for the red-fluorescing tenascin-coated Covaspheres (left) or the green-fluorescing aggrecan-coated Covaspheres (right). In addition, no co-aggregation was detected between the red and green fluorescing Covaspheres. Thus, tenascin binding to 3F8 PG is not due to merely an indiscriminate affinity for proteoglycan molecules, but is specific for, at a minimum, this class of RPTPase molecules. The specificity of the 3F8/tenascin interaction is further demonstrated when tenascin-coated Covaspheres are mixed with Ng-CAM-coated Covaspheres. As shown in FIG. 15, Panel 4, red-fluorescing tenascin-coated Covaspheres (left) segregate independent of green-fluorescing Ng-CAM fluorescing Covaspheres, indicating that tenascin does not bind Ng-CAM, another molecule which has been shown to be a ligand for 3F8 (see Section 7, above). Note that, as has been noted previously (Grumet, M. and Edelman, G. M., 1988, J. Cell Biol. 106: 487–503), Ng-CAM has the ability to self-aggregate, explaining the Ng-CAM-gated Covaspheres aggregation in the present experiment (FIG. 15, Panel 4, right).

It is apparent that many modifications and variations of this invention as set forth here may be made without departing from the spirit and scope thereof. The specific embodiments described hereinabove are given by way of example only and the invention is limited only by the terms of the appended claims.

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
       (A) LENGTH: 11 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= Xaa
           /note= "Xaa = Ile or Val"

(ix) FEATURE:
       (A) NAME/KEY: Modified-site
       (B) LOCATION: 4
       (D) OTHER INFORMATION: /label= Xaa
           /note= "Xaa = Any amino acid"

(ix) FEATURE:
       (A) NAME/KEY: Modified-site
       (B) LOCATION: 7..8
       (D) OTHER INFORMATION: /label= Xaa
           /note= "Xaa = Any amino acid"

(ix) FEATURE:
       (A) NAME/KEY: Modified-site
       (B) LOCATION: 10
       (D) OTHER INFORMATION: /label= Xaa
           /note= "Xaa = Ser or Thr"

(xi) SEQUENCE DESCRIPTION: SEQ ID NO: 1:

Xaa His Cys Xaa Ala Gly Xaa Xaa Arg Xaa Gly
1               5                   10

(2) INFORMATION FOR SEQ ID NO: 2:

(i) SEQUENCE CHARACTERISTICS:
       (A) LENGTH: 2308 amino acids
       (B) TYPE: amino acid
       (C) STRANDEDNESS: single
       (D) TOPOLOGY: unknown (ii) MOLECULE TYPE: protein (xi) SEQUENCE DESCRIPTION: SEQ ID NO: 2:

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val

-continued

```
                100                 105                 110
Ser Gly Gly Val Ser Glu Met Val Phe Lys Ala Ser Lys Ile Thr Phe
        115                 120                 125
His Trp Gly Lys Cys Asn Met Ser Ser Asp Gly Ser Glu His Ser Leu
        130                 135             140
Glu Gly Gln Lys Phe Pro Leu Glu Met Gln Ile Tyr Cys Phe Asp Ala
145                 150                 155                 160
Asp Arg Phe Ser Ser Phe Glu Ala Val Lys Gly Lys Gly Lys Leu
                165                 170                 175
Arg Ala Leu Ser Ile Leu Phe Glu Val Gly Thr Glu Glu Asn Leu Asp
            180                 185                 190
Phe Lys Ala Ile Ile Asp Gly Val Glu Ser Val Ser Arg Phe Gly Lys
        195                 200                 205
Gln Ala Ala Leu Asp Pro Phe Ile Leu Leu Asn Leu Leu Pro Asn Ser
        210                 215                 220
Thr Asp Lys Tyr Tyr Ile Tyr Asn Gly Ser Leu Thr Ser Pro Pro Cys
225                 230                 235                 240
Thr Asp Thr Val Asp Trp Ile Val Phe Lys Asp Thr Val Ser Ile Ser
                245                 250                 255
Glu Ser Gln Leu Ala Val Phe Cys Glu Val Leu Thr Met Gln Gln Ser
            260                 265                 270
Gly Tyr Val Met Leu Met Asp Tyr Leu Gln Asn Asn Phe Arg Glu Gln
        275                 280                 285
Gln Tyr Lys Phe Ser Arg Gln Val Phe Ser Ser Tyr Thr Gly Lys Glu
        290                 295                 300
Glu Ile His Glu Ala Val Cys Ser Ser Glu Pro Glu Asn Val Gln Ala
305                 310                 315                 320
Asp Pro Glu Asn Tyr Thr Ser Leu Leu Val Thr Trp Glu Arg Pro Arg
                325                 330                 335
Val Val Tyr Asp Thr Met Ile Glu Lys Phe Ala Val Leu Tyr Gln Gln
            340                 345                 350
Leu Asp Gly Glu Asp Gln Thr Lys His Glu Phe Leu Thr Asp Gly Tyr
        355                 360                 365
Gln Asp Leu Gly Ala Ile Leu Asn Asn Leu Leu Pro Asn Met Ser Tyr
        370                 375                 380
Val Leu Gln Ile Val Ala Ile Cys Thr Asn Gly Leu Tyr Gly Lys Tyr
385                 390                 395                 400
Ser Asp Gln Leu Ile Val Asp Met Pro Thr Asp Asn Pro Glu Leu Asp
                405                 410                 415
Leu Phe Pro Glu Leu Ile Gly Thr Glu Glu Ile Ile Lys Glu Glu Glu
            420                 425                 430
Glu Gly Lys Asp Ile Glu Glu Gly Ala Ile Val Asn Pro Gly Arg Asp
        435                 440                 445
Ser Ala Thr Asn Gln Ile Arg Lys Lys Glu Pro Gln Ile Ser Thr Thr
        450                 455                 460
Thr His Tyr Asn Arg Ile Gly Thr Lys Tyr Asn Glu Ala Lys Thr Asn
465                 470                 475                 480
Arg Ser Pro Thr Arg Gly Ser Glu Phe Ser Gly Lys Gly Asp Val Pro
                485                 490                 495
Asn Thr Ser Leu Asn Ser Thr Ser Gln Pro Val Thr Lys Leu Ala Thr
            500                 505                 510
Glu Lys Asp Ile Ser Leu Thr Ser Gln Thr Val Thr Glu Leu Pro Pro
        515                 520                 525
```

```
His Thr Val Glu Gly Thr Ser Ala Ser Leu Asn Asp Gly Ser Lys Thr
    530                 535                 540
Val Leu Arg Ser Pro His Met Asn Leu Ser Gly Thr Ala Glu Ser Leu
545                 550                 555                 560
Asn Thr Val Ser Ile Thr Glu Tyr Glu Glu Glu Ser Leu Leu Thr Ser
                565                 570                 575
Phe Lys Leu Asp Thr Gly Ala Glu Asp Ser Ser Gly Ser Ser Pro Ala
            580                 585                 590
Thr Ser Ala Ile Pro Phe Ile Ser Glu Asn Ile Ser Gln Gly Tyr Ile
        595                 600                 605
Phe Ser Ser Glu Asn Pro Glu Thr Ile Thr Tyr Asp Val Leu Ile Pro
    610                 615                 620
Glu Ser Ala Arg Asn Ala Ser Glu Asp Ser Thr Ser Ser Gly Ser Glu
625                 630                 635                 640
Glu Ser Leu Lys Asp Pro Ser Met Glu Gly Asn Val Trp Phe Pro Ser
                645                 650                 655
Ser Thr Asp Ile Thr Ala Gln Pro Asp Val Gly Ser Gly Arg Glu Ser
            660                 665                 670
Phe Leu Gln Thr Asn Tyr Thr Glu Ile Arg Val Asp Glu Ser Glu Lys
        675                 680                 685
Thr Thr Lys Ser Phe Ser Ala Gly Pro Val Met Ser Gln Gly Pro Ser
    690                 695                 700
Val Thr Asp Leu Glu Met Pro His Tyr Ser Thr Phe Ala Tyr Phe Pro
705                 710                 715                 720
Thr Glu Val Thr Pro His Ala Phe Thr Pro Ser Ser Arg Gln Gln Asp
                725                 730                 735
Leu Val Ser Thr Val Asn Val Val Tyr Ser Gln Thr Thr Gln Pro Val
            740                 745                 750
Tyr Asn Gly Glu Thr Pro Leu Gln Pro Ser Tyr Ser Ser Glu Val Phe
        755                 760                 765
Pro Leu Val Thr Pro Leu Leu Leu Asp Asn Gln Ile Leu Asn Thr Thr
    770                 775                 780
Pro Ala Ala Ser Ser Ser Asp Ser Ala Leu His Ala Thr Pro Val Phe
785                 790                 795                 800
Pro Ser Val Asp Val Ser Phe Glu Ser Ile Leu Ser Ser Tyr Asp Gly
                805                 810                 815
Ala Pro Leu Leu Pro Phe Ser Ser Ala Ser Phe Ser Ser Glu Leu Phe
            820                 825                 830
Arg His Leu His Thr Val Ser Gln Ile Leu Pro Gln Val Thr Ser Ala
        835                 840                 845
Thr Glu Ser Asp Lys Val Pro Leu His Ala Ser Leu Pro Val Ala Gly
    850                 855                 860
Gly Asp Leu Leu Leu Glu Pro Ser Leu Ala Gln Tyr Ser Asp Val Leu
865                 870                 875                 880
Ser Thr Thr His Ala Ala Ser Lys Thr Leu Glu Phe Gly Ser Glu Ser
                885                 890                 895
Gly Val Leu Tyr Lys Thr Leu Met Phe Ser Gln Val Glu Pro Pro Ser
            900                 905                 910
Ser Asp Ala Met Met His Ala Arg Ser Ser Gly Pro Glu Pro Ser Tyr
        915                 920                 925
Ala Leu Ser Asp Asn Glu Gly Ser Gln His Ile Phe Thr Val Ser Tyr
    930                 935                 940
```

-continued

```
Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
            965                 970                 975

Ile Thr Pro Thr Ala Ser Leu Leu Gln Pro Thr His Ala Leu Ser Gly
        980                 985                 990

Asp Gly Glu Trp Ser Gly Ala Ser Ser Asp Ser Glu Phe Leu Leu Pro
    995                 1000                1005

Asp Thr Asp Gly Leu Thr Ala Leu Asn Ile Ser Ser Pro Val Ser Val
    1010                1015                1020

Ala Glu Phe Thr Tyr Thr Thr Ser Val Phe Gly Asp Asp Asn Lys Ala
1025                1030                1035                1040

Leu Ser Lys Ser Glu Ile Ile Tyr Gly Asn Glu Thr Glu Leu Gln Ile
                1045                1050                1055

Pro Ser Phe Asn Glu Met Val Tyr Pro Ser Glu Ser Thr Val Met Pro
            1060                1065                1070

Asn Met Tyr Asp Asn Val Asn Lys Leu Asn Ala Ser Leu Gln Glu Thr
        1075                1080                1085

Ser Val Ser Ile Ser Ser Thr Lys Gly Met Phe Pro Gly Ser Leu Ala
    1090                1095                1100

His Thr Thr Thr Lys Val Phe Asp His Glu Ile Ser Gln Val Pro Glu
1105                1110                1115                1120

Asn Asn Phe Ser Val Gln Pro Thr His Thr Val Ser Gln Ala Ser Gly
                1125                1130                1135

Asp Thr Ser Leu Lys Pro Val Leu Ser Ala Asn Ser Glu Pro Ala Ser
            1140                1145                1150

Ser Asp Pro Ala Ser Ser Glu Met Leu Ser Pro Ser Thr Gln Leu Leu
        1155                1160                1165

Phe Tyr Glu Thr Ser Ala Ser Phe Ser Thr Glu Val Leu Leu Gln Pro
    1170                1175                1180

Ser Phe Gln Ala Ser Asp Val Asp Thr Leu Leu Lys Thr Val Leu Pro
1185                1190                1195                1200

Ala Val Pro Ser Asp Pro Ile Leu Val Glu Thr Pro Lys Val Asp Lys
                1205                1210                1215

Ile Ser Ser Thr Met Leu His Leu Ile Val Ser Asn Ser Ala Ser Ser
            1220                1225                1230

Glu Asn Met Leu His Ser Thr Ser Val Pro Val Phe Asp Val Ser Pro
        1235                1240                1245

Thr Ser His Met His Ser Ala Ser Leu Gln Gly Leu Thr Ile Ser Tyr
    1250                1255                1260

Ala Ser Glu Lys Tyr Glu Pro Val Leu Leu Lys Ser Glu Ser Ser His
1265                1270                1275                1280

Gln Val Val Pro Ser Leu Tyr Ser Asn Asp Glu Leu Phe Gln Thr Ala
                1285                1290                1295

Asn Leu Glu Ile Asn Gln Ala His Pro Pro Lys Gly Arg His Val Phe
            1300                1305                1310

Ala Thr Pro Val Leu Ser Ile Asp Glu Pro Leu Asn Thr Leu Ile Asn
        1315                1320                1325

Lys Leu Ile His Ser Asp Glu Ile Leu Thr Ser Thr Lys Ser Ser Val
    1330                1335                1340

Thr Gly Lys Val Phe Ala Gly Ile Pro Thr Val Ala Ser Asp Thr Phe
1345                1350                1355                1360

Val Ser Thr Asp His Ser Val Pro Ile Gly Asn Gly His Val Ala Ile
```

-continued

```
                1365                1370                1375
Thr Ala Val Ser Pro His Arg Asp Gly Ser Val Thr Ser Thr Lys Leu
            1380                1385                1390
Leu Phe Pro Ser Lys Ala Thr Ser Glu Leu Ser His Ser Ala Lys Ser
        1395                1400                1405
Asp Ala Gly Leu Val Gly Gly Gly Glu Asp Gly Asp Thr Asp Asp Asp
    1410                1415                1420
Gly Asp Asp Asp Asp Asp Arg Gly Ser Asp Gly Leu Ser Ile His
1425                1430                1435                1440
Lys Cys Met Ser Cys Ser Ser Tyr Arg Glu Ser Gln Glu Lys Val Met
            1445                1450                1455
Asn Asp Ser Asp Thr His Glu Asn Ser Leu Met Asp Gln Asn Asn Pro
        1460                1465                1470
Ile Ser Tyr Ser Leu Ser Glu Asn Ser Glu Glu Asp Asn Arg Val Thr
    1475                1480                1485
Ser Val Ser Ser Asp Ser Gln Thr Gly Met Asp Arg Ser Pro Gly Lys
        1490                1495                1500
Ser Pro Ser Ala Asn Gly Leu Ser Gln Lys His Asn Asp Gly Lys Glu
1505                1510                1515                1520
Glu Asn Asp Ile Gln Thr Gly Ser Ala Leu Leu Pro Leu Ser Pro Glu
            1525                1530                1535
Ser Lys Ala Trp Ala Val Leu Thr Ser Asp Glu Glu Ser Gly Ser Gly
        1540                1545                1550
Gln Gly Thr Ser Asp Ser Leu Asn Glu Asn Glu Thr Ser Thr Asp Phe
    1555                1560                1565
Ser Phe Ala Asp Thr Asn Glu Lys Asp Ala Asp Gly Ile Leu Ala Ala
        1570                1575                1580
Gly Asp Ser Glu Ile Thr Pro Gly Phe Pro Gln Ser Pro Thr Ser Ser
1585                1590                1595                1600
Val Thr Ser Glu Asn Ser Glu Val Phe His Val Ser Glu Ala Glu Ala
            1605                1610                1615
Ser Asn Ser Ser His Glu Ser Arg Ile Gly Leu Ala Glu Gly Leu Glu
        1620                1625                1630
Ser Glu Lys Lys Ala Val Ile Pro Leu Val Ile Val Ser Ala Leu Thr
    1635                1640                1645
Phe Ile Cys Leu Val Val Leu Val Gly Ile Leu Ile Tyr Trp Arg Lys
        1650                1655                1660
Cys Phe Gln Thr Ala His Phe Tyr Leu Glu Asp Ser Thr Ser Pro Arg
1665                1670                1675                1680
Val Ile Ser Thr Pro Pro Thr Pro Ile Phe Pro Ile Ser Asp Asp Val
            1685                1690                1695
Gly Ala Ile Pro Ile Lys His Phe Pro Lys His Val Ala Asp Leu His
        1700                1705                1710
Ala Ser Ser Gly Phe Thr Glu Glu Phe Glu Glu Val Gln Ser Cys Thr
        1715                1720                1725
Val Asp Leu Gly Ile Thr Ala Asp Ser Ser Asn His Pro Asp Asn Lys
    1730                1735                1740
His Lys Asn Arg Tyr Ile Asn Ile Val Ala Tyr Asp His Ser Arg Val
1745                1750                1755                1760
Lys Leu Ala Gln Leu Ala Glu Lys Asp Gly Lys Leu Thr Asp Tyr Ile
            1765                1770                1775
Asn Ala Asn Tyr Val Asp Gly Tyr Asn Arg Pro Lys Ala Tyr Ile Ala
        1780                1785                1790
```

-continued

Ala Gln Gly Pro Leu Lys Ser Thr Ala Glu Asp Phe Trp Arg Met Ile
        1795                1800                1805

Trp Glu His Asn Val Glu Val Ile Val Met Ile Thr Asn Leu Val Glu
    1810                1815                1820

Lys Gly Arg Arg Lys Cys Asp Gln Tyr Trp Pro Ala Asp Gly Ser Glu
1825                1830                1835                1840

Glu Tyr Gly Asn Phe Leu Val Thr Gln Lys Ser Val Gln Val Leu Ala
        1845                1850                1855

Tyr Tyr Thr Val Arg Asn Phe Thr Leu Arg Asn Thr Lys Ile Lys Lys
            1860                1865                1870

Gly Ser Gln Lys Gly Arg Pro Ser Gly Arg Val Val Thr Gln Tyr His
        1875                1880                1885

Tyr Thr Gln Trp Pro Asp Met Gly Val Pro Glu Tyr Ser Leu Pro Val
        1890                1895                1900

Leu Thr Phe Val Arg Lys Ala Ala Tyr Ala Lys Arg His Ala Val Gly
1905                1910                1915                1920

Pro Val Val Val His Cys Ser Ala Gly Val Gly Arg Thr Gly Thr Tyr
            1925                1930                1935

Ile Val Leu Asp Ser Met Leu Gln Gln Ile Gln His Glu Gly Thr Val
        1940                1945                1950

Asn Ile Phe Gly Phe Leu Lys His Ile Arg Ser Gln Arg Asn Tyr Leu
        1955                1960                1965

Val Gln Thr Glu Glu Gln Tyr Val Phe Ile His Asp Thr Leu Val Glu
    1970                1975                1980

Ala Ile Leu Ser Lys Glu Thr Glu Val Leu Asp Ser His Ile His Ala
1985                1990                1995                2000

Tyr Val Asn Ala Leu Leu Ile Pro Gly Pro Ala Gly Lys Thr Lys Leu
            2005                2010                2015

Glu Lys Gln Phe Gln Leu Leu Ser Gln Ser Asn Ile Gln Gln Ser Asp
        2020                2025                2030

Tyr Ser Ala Ala Leu Lys Gln Cys Asn Arg Glu Lys Asn Arg Thr Ser
        2035                2040                2045

Ser Ile Ile Pro Val Glu Arg Ser Arg Val Gly Ile Ser Ser Leu Ser
2050                2055                2060

Gly Glu Gly Thr Asp Tyr Ile Asn Ala Ser Tyr Ile Met Gly Tyr Tyr
2065                2070                2075                2080

Gln Ser Asn Glu Phe Ile Ile Thr Gln His Pro Leu Leu His Thr Ile
        2085                2090                2095

Lys Asp Phe Trp Arg Met Ile Trp Asp His Asn Ala Gln Leu Val Val
        2100                2105                2110

Met Ile Pro Asp Gly Gln Asn Met Ala Glu Asp Glu Phe Val Tyr Trp
    2115                2120                2125

Pro Asn Lys Asp Glu Pro Ile Asn Cys Glu Ser Phe Lys Val Thr Leu
        2130                2135                2140

Met Ala Glu Glu His Lys Cys Leu Ser Asn Glu Glu Lys Leu Ile Ile
2145                2150                2155                2160

Gln Asp Phe Ile Leu Glu Ala Thr Gln Asp Asp Tyr Val Leu Glu Val
            2165                2170                2175

Arg His Phe Gln Cys Pro Lys Trp Pro Asn Pro Asp Ser Pro Ile Ser
        2180                2185                2190

Lys Thr Phe Glu Leu Ile Ser Val Ile Lys Glu Glu Ala Ala Asn Arg
        2195                2200                2205

```
Asp Gly Pro Met Ile Val His Asp Glu His Gly Val Thr Ala Gly
           2210                2215               2220

Thr Phe Cys Ala Leu Thr Thr Leu Met His Gln Leu Glu Lys Glu Asn
2225            2230            2235             2240

Ser Val Asp Val Tyr Gln Val Ala Lys Met Ile Asn Leu Met Arg Pro
                2245            2250            2255

Gly Val Phe Ala Asp Ile Glu Gln Tyr Gln Phe Leu Tyr Lys Val Ile
                2260            2265            2270

Leu Ser Leu Val Ser Thr Arg Gln Glu Glu Asn Pro Ser Thr Ser Leu
                2275            2280            2285

Asp Ser Asn Gly Ala Ala Leu Pro Asp Gly Asn Ile Ala Glu Ser Leu
                2290            2295            2300

Glu Ser Leu Val
2305

(2) INFORMATION FOR SEQ ID NO: 3:

(i) SEQUENCE CHARACTERISTICS:
        (A) LENGTH: 267 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 3:

Gly Asp Pro Tyr Trp Ala Tyr Ser Gly Ala Tyr Gly Pro Glu His Trp
1               5               10              15

Val Thr Ser Val Ser Cys Gly Gly Arg His Gln Ser Pro Ile Asp
            20              25              30

Ile Leu Asp Gln Tyr Ala Arg Val Gly Glu Glu Tyr Gln Glu Leu Gln
            35              40              45

Leu Asp Gly Phe Asp Asn Glu Ser Ser Asn Lys Thr Trp Met Lys Asn
50              55              60

Thr Gly Lys Thr Val Ala Ile Leu Leu Lys Asp Asp Tyr Phe Val Ser
65              70              75              80

Gly Ala Gly Leu Pro Gly Arg Phe Lys Ala Glu Lys Val Glu Phe His
                85              90              95

Trp Gly His Ser Asn Gly Ser Ala Gly Ser Glu His Ser Ile Asn Gly
                100             105             110

Arg Arg Phe Pro Val Glu Met Gln Ile Phe Phe Tyr Asn Pro Asp Asp
            115             120             125

Phe Asp Ser Phe Gln Thr Ala Ile Ser Glu Asn Arg Ile Ile Gly Ala
130             135             140

Met Ala Ile Phe Phe Gln Val Ser Pro Arg Asp Asn Ser Ala Leu Asp
145             150             155             160

Pro Ile Ile His Gly Leu Lys Gly Val Val His His Glu Lys Glu Thr
                165             170             175

Phe Leu Asp Pro Phe Val Leu Arg Asp Leu Leu Pro Ala Ser Leu Gly
            180             185             190

Ser Tyr Tyr Arg Tyr Thr Gly Ser Leu Thr Thr Pro Pro Cys Ser Glu
            195             200             205

Ile Val Glu Trp Ile Val Phe Arg Arg Pro Val Pro Ile Ser Tyr His
            210             215             220

Gln Leu Glu Ala Phe Tyr Ser Ile Phe Thr Thr Glu Gln Gln Asp His
225             230             235             240
```

```
Val Lys Ser Val Glu Tyr Leu Arg Asn Asn Phe Arg Pro Gln Gln Arg
            245                 250                 255

Leu His Asp Arg Val Val Ser Lys Ser Ala Val
            260                 265

(2) INFORMATION FOR SEQ ID NO: 4:

(i) SEQUENCE CHARACTERISTICS:
        (A) LENGTH: 260 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 4:

Ala Ser Pro Asp Trp Gly Tyr Asp Asp Lys Asn Gly Pro Glu Gln Trp
1               5                   10                  15

Ser Lys Leu Tyr Pro Ile Ala Asn Gly Asn Asn Gln Ser Pro Val Asp
            20                  25                  30

Ile Lys Thr Ser Glu Thr Lys His Asp Thr Ser Leu Lys Pro Ile Ser
            35                  40                  45

Val Ser Tyr Asn Pro Ala Thr Ala Lys Glu Ile Ile Asn Val Gly His
            50                  55                  60

Ser Phe His Val Asn Phe Glu Asp Asn Asp Asn Arg Ser Val Leu Lys
65                      70                  75                  80

Gly Gly Pro Phe Ser Asp Ser Tyr Arg Leu Phe Gln Phe His Phe His
                    85                  90                  95

Trp Gly Ser Thr Asn Glu His Gly Ser Glu His Thr Val Asp Gly Val
                    100                 105                 110

Lys Tyr Ser Ala Glu Leu His Val Ala His Trp Asn Ser Ala Lys Tyr
            115                 120                 125

Ser Ser Leu Ala Glu Ala Ala Ser Lys Ala Asp Gly Leu Ala Val Ile
            130                 135                 140

Gly Val Leu Met Lys Val Gly Glu Ala Asn Pro Lys Leu Gln Lys Val
145                 150                 155                 160

Leu Asp Ala Leu Gln Ala Ile Lys Thr Lys Gly Lys Arg Ala Pro Phe
                    165                 170                 175

Thr Asn Phe Asp Pro Ser Thr Leu Leu Pro Ser Ser Leu Asp Phe Trp
                    180                 185                 190

Thr Tyr Pro Gly Ser Leu Thr His Pro Pro Leu Tyr Glu Ser Val Thr
            195                 200                 205

Trp Ile Ile Cys Lys Glu Ser Ile Ser Val Ser Ser Glu Gln Leu Ala
            210                 215                 220

Gln Phe Arg Ser Leu Leu Ser Asn Val Glu Gly Asp Asn Ala Val Pro
225                 230                 235                 240

Met Gln His Asn Asn Arg Pro Thr Gln Pro Leu Lys Gly Arg Thr Val
                    245                 250                 255

Arg Ala Ser Phe
            260

(2) INFORMATION FOR SEQ ID NO: 5:

(i) SEQUENCE CHARACTERISTICS:
        (A) LENGTH: 259 amino acids
        (B) TYPE: amino acid
        (C) STRANDEDNESS: single
        (D) TOPOLOGY: unknown
```

-continued (ii) MOLECULE TYPE: protein (xi) SEQUENCE DESCRIPTION: SEQ ID NO: 5:

```
Ser His His Trp Gly Tyr Gly Lys His Asn Gly Pro Glu His Trp His
1               5                   10                  15

Lys Asp Phe Pro Ile Ala Lys Gly Glu Arg Gln Ser Pro Val Asp Ile
                20                  25                  30

Asp Thr His Thr Ala Lys Tyr Asp Pro Ser Leu Lys Pro Leu Ser Val
            35                  40                  45

Ser Tyr Asp Gln Ala Thr Ser Leu Arg Ile Leu Asn Asn Gly His Ala
    50                  55                  60

Phe Asn Val Glu Phe Asp Asp Ser Gln Asp Lys Ala Val Leu Lys Gly
65                  70                  75                  80

Gly Pro Leu Asp Gly Thr Tyr Arg Leu Ile Gln Phe His Phe His Trp
                85                  90                  95

Gly Ser Leu Asp Gly Gln Gly Ser Glu His Thr Val Asp Lys Lys Lys
                100                 105                 110

Tyr Ala Ala Glu Leu His Leu Val His Trp Asn Thr Lys Tyr Gly Asp
            115                 120                 125

Phe Gly Lys Ala Val Gln Gln Pro Asp Gly Leu Ala Val Leu Gly Ile
    130                 135                 140

Phe Leu Lys Val Gly Ser Ala Lys Pro Gly Leu Gln Lys Val Val Asp
145                 150                 155                 160

Val Leu Asp Ser Ile Lys Thr Lys Gly Lys Ser Ala Asp Phe Thr Asn
                165                 170                 175

Phe Asp Pro Arg Gly Leu Leu Pro Glu Ser Leu Asp Tyr Trp Thr Tyr
            180                 185                 190

Pro Gly Ser Leu Thr Thr Pro Pro Leu Leu Glu Cys Val Thr Trp Ile
    195                 200                 205

Val Leu Lys Glu Pro Ile Ser Val Ser Ser Glu Gln Val Leu Lys Phe
210                 215                 220

Arg Lys Leu Asn Phe Asn Gly Glu Gly Glu Pro Glu Glu Leu Met Val
225                 230                 235                 240

Asp Asn Trp Arg Pro Ala Gln Pro Leu Lys Asn Arg Gln Ile Lys Ala
                245                 250                 255

Ser Phe Lys
```

(2) INFORMATION FOR SEQ ID NO: 6:

(i) SEQUENCE CHARACTERISTICS:
       (A) LENGTH: 259 amino acids
       (B) TYPE: amino acid
       (C) STRANDEDNESS: single
       (D) TOPOLOGY: unknown (ii) MOLECULE TYPE: protein (xi) SEQUENCE DESCRIPTION: SEQ ID NO: 6:

```
Ala Lys Glu Trp Gly Tyr Ala Ser His Asn Gly Pro Asp His Trp His
1               5                   10                  15

Glu Leu Phe Pro Asn Ala Lys Gly Glu Asn Gln Ser Pro Ile Glu Leu
                20                  25                  30

His Thr Lys Asp Ile Arg His Asp Pro Ser Leu Gln Pro Trp Ser Val
            35                  40                  45

Ser Tyr Asp Gly Gly Ser Ala Lys Thr Ile Leu Asn Asn Gly Lys Thr
    50                  55                  60
```

-continued

```
Cys Arg Val Val Phe Asp Asp Thr Tyr Asp Arg Ser Met Leu Arg Gly
 65                  70                  75                  80

Gly Pro Leu Pro Gly Pro Tyr Arg Leu Arg Gln Phe His Leu His Trp
                 85                  90                  95

Gly Ser Ser Asp Asp His Gly Ser Glu His Thr Val Asp Gly Val Lys
            100                 105                 110

Tyr Ala Ala Glu Leu His Leu Val His Trp Asn Pro Lys Tyr Asn Thr
        115                 120                 125

Phe Lys Glu Ala Leu Lys Gln Arg Asp Gly Ile Ala Val Ile Gly Ile
    130                 135                 140

Phe Leu Lys Ile Gly His Glu Asn Gly Glu Phe Gln Ile Phe Leu Asp
145                 150                 155                 160

Ala Leu Asp Lys Ile Lys Thr Lys Gly Lys Glu Ala Pro Phe Thr Lys
                165                 170                 175

Phe Asp Pro Ser Cys Leu Phe Pro Ala Cys Arg Asp Tyr Trp Thr Tyr
            180                 185                 190

Gln Gly Ser Phe Thr Thr Pro Pro Cys Glu Glu Cys Ile Val Trp Leu
        195                 200                 205

Leu Leu Lys Glu Pro Met Thr Val Ser Ser Asp Gln Met Ala Lys Leu
    210                 215                 220

Arg Ser Leu Leu Ser Ser Ala Glu Asn Glu Pro Pro Val Pro Leu Val
225                 230                 235                 240

Ser Asn Trp Arg Pro Pro Gln Pro Ile Asn Asn Arg Val Val Arg Ala
                245                 250                 255

Ser Phe Lys (2) INFORMATION FOR SEQ ID NO: 7:

(i) SEQUENCE CHARACTERISTICS:
        (A) LENGTH: 268 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 7:

Ala Glu Ser His Trp Cys Tyr Glu Val Gln Ala Glu Ser Ser Asn Tyr
 1               5                  10                  15

Pro Cys Leu Val Pro Val Lys Trp Gly Gly Asn Cys Gln Lys Asp Arg
                 20                  25                  30

Gln Ser Pro Ile Asn Ile Val Thr Thr Lys Ala Lys Val Asp Lys Lys
             35                  40                  45

Leu Gly Arg Phe Phe Phe Ser Gly Tyr Asp Lys Lys Gln Thr Trp Thr
 50                  55                  60

Val Gln Asn Asn Gly His Ser Val Met Met Leu Leu Glu Asn Lys Ala
 65                  70                  75                  80

Ser Ile Ser Gly Gly Gly Leu Pro Ala Pro Tyr Gln Ala Lys Gln Leu
                 85                  90                  95

His Leu His Trp Ser Asp Leu Pro Tyr Lys Gly Ser Glu His Ser Leu
            100                 105                 110

Asp Gly Glu His Phe Ala Met Glu Met His Ile Val His Glu Lys Glu
        115                 120                 125

Lys Gly Thr Ser Arg Asn Val Lys Glu Ala Gln Asp Pro Glu Asp Glu
    130                 135                 140

Ile Ala Val Leu Ala Phe Leu Val Glu Ala Gly Thr Gln Val Asn Glu
```

```
            145                 150                 155                 160
Gly Phe Gln Pro Leu Val Glu Ala Leu Ser Asn Ile Pro Lys Pro Glu
                165                 170                 175

Met Ser Thr Thr Met Ala Glu Ser Ser Leu Leu Asp Leu Leu Pro Lys
                180                 185                 190

Glu Glu Lys Leu Arg His Tyr Phe Arg Tyr Leu Gly Ser Leu Thr Thr
                195                 200                 205

Pro Thr Cys Asp Glu Lys Val Val Trp Thr Val Phe Arg Glu Pro Ile
            210                 215                 220

Gln Leu His Arg Glu Gln Ile Leu Ala Phe Ser Gln Lys Leu Tyr Tyr
225                 230                 235                 240

Asp Lys Glu Gln Thr Val Ser Met Lys Asp Asn Val Arg Pro Leu Gln
                245                 250                 255

Gln Leu Gly Gln Arg Thr Val Ile Lys Ser Gly Ala
                260                 265

(2) INFORMATION FOR SEQ ID NO: 8:

(i) SEQUENCE CHARACTERISTICS:
        (A) LENGTH: 262 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 8:

Gln His Val Ser Asp Trp Thr Tyr Ser Glu Gly Ala Leu Asp Glu Ala
1               5                   10                  15

His Trp Pro Gln His Tyr Pro Ala Cys Gly Gly Gln Arg Gln Ser Pro
                20                  25                  30

Ile Asn Leu Gln Arg Thr Lys Val Arg Tyr Asn Pro Ser Leu Lys Gly
            35                  40                  45

Leu Asn Met Thr Gly Tyr Glu Thr Gln Ala Gly Glu Phe Pro Met Val
50                  55                  60

Asn Asn Gly His Thr Val Gln Ile Gly Leu Pro Ser Thr Met Arg Met
65                  70                  75                  80

Thr Val Ala Asp Gly Ile Val Tyr Ile Ala Gln Gln Met His Phe His
                85                  90                  95

Trp Gly Gly Ala Ser Ser Glu Ile Ser Gly Ser Glu His Thr Val Asp
                100                 105                 110

Gly Ile Arg His Val Ile Glu Ile His Ile Val His Tyr Asn Ser Lys
            115                 120                 125

Tyr Lys Thr Tyr Asp Ile Ala Gln Asp Ala Pro Asp Gly Leu Ala Val
            130                 135                 140

Leu Ala Ala Phe Val Glu Val Lys Asn Tyr Pro Glu Asn Thr Tyr Tyr
145                 150                 155                 160

Ser Asn Phe Ile Ser His Leu Ala Asn Ile Lys Tyr Pro Gly Gln Arg
                165                 170                 175

Thr Thr Leu Thr Gly Leu Asp Val Gln Asp Met Leu Pro Arg Asn Leu
                180                 185                 190

Gln His Tyr Tyr Thr Tyr His Gly Ser Leu Thr Thr Pro Pro Cys Thr
            195                 200                 205

Glu Asn Val His Trp Phe Val Leu Ala Asp Phe Val Lys Leu Ser Arg
            210                 215                 220

Thr Gln Val Trp Lys Leu Glu Asn Ser Leu Leu Asp His Arg Asn Lys
```

-continued

```
               225                 230                 235                 240
Thr Ile His Asn Asp Tyr Arg Arg Thr Gln Pro Leu Asn His Arg Val
                245                 250                 255
Val Glu Ser Asn Phe Pro
                260

(2) INFORMATION FOR SEQ ID NO: 9:

(i) SEQUENCE CHARACTERISTICS:
        (A) LENGTH: 261 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 9:

Gly His His Gly Trp Gly Tyr Gly Gln Asp Asp Gly Pro Ala Ser His
1               5                  10                  15

Trp His Lys Leu Tyr Pro Ile Ala Gln Gly Asp Arg Gln Ser Pro Ile
                20                  25                  30

Asn Ile Ile Ser Ser Gln Ala Val Tyr Ser Pro Ser Leu Gln Pro Leu
                35                  40                  45

Glu Leu Ser Tyr Glu Ala Cys Met Ser Leu Ser Ile Thr Asn Asn Gly
 50                 55                  60

His Ser Val Gln Val Asp Phe Asn Asp Ser Asp Asp Arg Thr Val Val
 65                 70                  75                  80

Thr Gly Gly Pro Leu Glu Gly Pro Tyr Arg Leu Lys Gln Phe His Phe
                85                  90                  95

His Trp Gly Lys Lys His Asp Val Gly Ser Glu His Thr Val Asp Gly
                100                 105                 110

Lys Ser Phe Pro Ser Glu Leu His Leu Val His Trp Asn Ala Lys Lys
                115                 120                 125

Tyr Ser Thr Phe Gly Glu Ala Ala Ser Ala Pro Asp Gly Leu Ala Val
                130                 135                 140

Gly Val Phe Leu Glu Thr Gly Asp Glu His Pro Ser Met Asn Arg Leu
145                 150                 155                 160

Thr Asp Ala Leu Tyr Met Val Arg Phe Lys Gly Thr Lys Ala Gln Phe
                165                 170                 175

Ser Cys Phe Asn Pro Lys Cys Leu Leu Pro Ala Ser Arg His Tyr Trp
                180                 185                 190

Thr Tyr Pro Gly Ser Leu Thr Thr Pro Pro Leu Ser Glu Ser Val Thr
                195                 200                 205

Trp Ile Val Leu Arg Glu Pro Ile Cys Ile Ser Glu Arg Gln Met Gly
                210                 215                 220

Lys Phe Arg Ser Leu Leu Phe Thr Ser Glu Asp Asp Glu Arg Ile His
225                 230                 235                 240

Met Val Asn Asn Phe Arg Pro Pro Gln Pro Leu Lys Gly Arg Val Val
                245                 250                 255

Lys Ala Ser Phe Arg
                260

(2) INFORMATION FOR SEQ ID NO: 10:

(i) SEQUENCE CHARACTERISTICS:
        (A) LENGTH: 260 amino acids
        (B) TYPE: amino acid
        (C) STRANDEDNESS: single
```

(D) TOPOLOGY: unknown (ii) MOLECULE TYPE: protein (xi) SEQUENCE DESCRIPTION: SEQ ID NO: 10:

Lys Leu Val Glu Glu Met Gly Trp Ser Tyr Thr Gly Ala Leu Asn Gln
1               5                   10                  15

Lys Asn Trp Gly Lys Lys Tyr Pro Ile Cys Asn Ser Pro Lys Gln Ser
            20                  25                  30

Pro Ile Asn Ile Asp Glu Asp Leu Thr Gln Val Asn Val Asn Leu Lys
            35                  40                  45

Lys Leu Lys Phe Gln Gly Trp Glu Lys Pro Ser Leu Glu Asn Thr Phe
    50                  55                  60

Ile His Asn Thr Gly Lys Thr Val Glu Ile Asn Leu Thr Asn Asp Tyr
65                  70                  75                  80

Tyr Leu Ser Gly Gly Leu Ser Glu Lys Val Phe Lys Ala Ser Lys Met
                85                  90                  95

Thr Phe His Trp Gly Lys Cys Asn Val Ser Ser Glu Gly Ser Glu His
                100                 105                 110

Ser Leu Glu Gly Gln Lys Phe Pro Leu Glu Met Gln Val Tyr Cys Phe
            115                 120                 125

Asp Ala Asp Arg Phe Ser Ser Phe Glu Glu Thr Val Lys Gly Lys Gly
130                 135                 140

Arg Leu Arg Ala Leu Ser Ile Leu Phe Glu Ile Gly Val Glu Glu Asn
145                 150                 155                 160

Leu Asp Tyr Lys Ala Ile Ile Asp Gly Thr Glu Ser Val Ser Arg Phe
                165                 170                 175

Gly Lys Gln Ala Ala Leu Asp Pro Phe Ile Leu Gln Asn Leu Leu Pro
            180                 185                 190

Asn Ser Thr Asp Lys Tyr Tyr Ile Tyr Asn Gly Ser Leu Thr Ser Pro
            195                 200                 205

Pro Cys Thr Asp Thr Val Glu Trp Ile Val Phe Lys Asp Thr Val Ser
    210                 215                 220

Ile Ser Glu Ser Gln Leu Pro Val Phe Cys Glu Val Leu Thr Met Gln
225                 230                 235                 240

Gln Ser Gly Tyr Val Met Leu Met Asp Tyr Leu Gln Asn Asn Phe Arg
                245                 250                 255

Glu Gln Gln Tyr
            260

(2) INFORMATION FOR SEQ ID NO: 11:

(i) SEQUENCE CHARACTERISTICS:
            (A) LENGTH: 4 amino acids
            (B) TYPE: amino acid
            (C) STRANDEDNESS: single
            (D) TOPOLOGY: unknown (ii) MOLECULE TYPE: peptide (ix) FEATURE:
            (A) NAME/KEY: Modified-site
            (B) LOCATION: 3
            (D) OTHER INFORMATION: /label= Xaa
                  /note= "Xaa = Any amino acid"

(xi) SEQUENCE DESCRIPTION: SEQ ID NO: 11:

Ser Gly Xaa Gly
1

```
(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /label= Xaa
              /note= "Xaa = Any amino acid"

(xi) SEQUENCE DESCRIPTION: SEQ ID NO: 12:

Asp Xaa Asn Asp Asn
1               5

(2) INFORMATION FOR SEQ ID NO: 13:

(i) SEQUENCE CHARACTERISTICS:
        (A) LENGTH: 4 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 13:

Asp Val Asn Glu
1
``` what is claimed is:

1. An isolated antibody that specifically binds the human RPTP-beta.

2. An antibody of claim 1, wherein said antibody is polyclonal.

3. An antibody of claim 1, wherein said antibody specifically binds to the segment of amino acids 2294–2308 of SEQ ID NO:2.

* * * * *